US010640817B2

(12) United States Patent
Nygren

(10) Patent No.: US 10,640,817 B2
(45) Date of Patent: May 5, 2020

(54) MULTIPLEX METHODS FOR DETECTION AND QUANTIFICATION OF MINOR VARIANTS

(71) Applicant: Agena Bioscience, Inc., San Diego, CA (US)

(72) Inventor: Anders Olof Herman Nygren, San Diego, CA (US)

(73) Assignee: Agena Bioscience, Inc., San Diego, CA (US)

( * ) Notice: Subject to any disclaimer, the term of this patent is extended or adjusted under 35 U.S.C. 154(b) by 145 days.

(21) Appl. No.: 15/568,701

(22) PCT Filed: Apr. 22, 2016

(86) PCT No.: PCT/US2016/028980
§ 371 (c)(1),
(2) Date: Oct. 23, 2017

(87) PCT Pub. No.: WO2016/172579
PCT Pub. Date: Oct. 27, 2016

(65) Prior Publication Data
US 2018/0298433 A1 Oct. 18, 2018

Related U.S. Application Data

(60) Provisional application No. 62/152,698, filed on Apr. 24, 2015.

(51) Int. Cl.
*C12Q 1/68* (2018.01)
*C12Q 1/6853* (2018.01)
*C12Q 1/6827* (2018.01)

(52) U.S. Cl.
CPC ......... *C12Q 1/6853* (2013.01); *C12Q 1/6827* (2013.01); *C12Q 2600/16* (2013.01)

(58) Field of Classification Search
None
See application file for complete search history.

(56) References Cited

U.S. PATENT DOCUMENTS

| | | |
|---|---|---|
| 4,515,781 A | 5/1985 | Torrence et al. |
| 4,582,789 A | 4/1986 | Sheldon, III et al. |
| 4,683,195 A | 7/1987 | Mullis et al. |
| 4,689,405 A | 8/1987 | Frank et al. |
| 4,711,955 A | 12/1987 | Ward et al. |
| 5,003,059 A | 3/1991 | Brennan |
| 5,013,830 A | 5/1991 | Ohtsuka et al. |
| 5,037,882 A | 8/1991 | Steel |
| 5,059,654 A | 10/1991 | Hou et al. |
| 5,064,754 A | 11/1991 | Mills |
| 5,118,605 A | 6/1992 | Urdea |
| 5,237,016 A | 8/1993 | Ghosh et al. |
| 5,242,974 A | 9/1993 | Holmes |
| 5,364,760 A | 11/1994 | Chu et al. |
| 5,380,833 A | 1/1995 | Urdea |
| 5,399,857 A | 3/1995 | Doroshenko et al. |
| 5,412,083 A | 5/1995 | Giese et al. |
| 5,480,784 A | 1/1996 | Kacian et al. |
| 5,489,507 A | 2/1996 | Chehab |
| 5,510,270 A | 4/1996 | Fodor et al. |
| 5,512,439 A | 4/1996 | Hornes et al. |
| 5,547,835 A | 8/1996 | Koster |
| 5,605,798 A | 2/1997 | Koster |
| 5,622,824 A | 4/1997 | Koster |
| 5,650,489 A | 7/1997 | Lam et al. |
| 5,691,141 A | 11/1997 | Koster |
| 5,700,642 A | 12/1997 | Monforte et al. |
| 5,710,028 A | 1/1998 | Eyal et al. |
| 5,770,272 A | 6/1998 | Biemann et al. |
| 5,800,984 A | 9/1998 | Vary |
| 5,851,765 A | 12/1998 | Koster |
| 5,869,242 A | 2/1999 | Kamb |
| 5,872,003 A | 2/1999 | Koster |
| 5,885,775 A | 3/1999 | Haff et al. |
| 5,888,819 A | 3/1999 | Goelet et al. |
| 5,925,520 A | 7/1999 | Tully et al. |
| 5,965,363 A | 10/1999 | Monforte et al. |
| 5,976,798 A | 11/1999 | Parker et al. |
| 5,989,871 A | 11/1999 | Grossman et al. |
| 6,004,744 A | 12/1999 | Goelet et al. |
| 6,043,031 A | 3/2000 | Koster |
| 6,074,823 A | 6/2000 | Koster |
| 6,194,144 B1 | 2/2001 | Koster |
| 6,197,498 B1 | 3/2001 | Koster |
| 6,221,601 B1 | 4/2001 | Koster et al. |
| 6,221,605 B1 | 4/2001 | Koster |
| 6,225,450 B1 | 5/2001 | Koster |

(Continued)

FOREIGN PATENT DOCUMENTS

| | | |
|---|---|---|
| CN | 103 131 787 | 6/2013 |
| EP | 0269520 | 1/1988 |

(Continued)

OTHER PUBLICATIONS

Mullis, Scientific American 262 (4), 56 (1990).*
Office Action dated Oct. 22, 2018 in U.S. Appl. No. 15/136,024, filed Apr. 22, 2016 and published as US 2016-0312278 on Oct. 27, 2016.
Office Action dated Nov. 16, 2018 in U.S. Appl. No. 13/126,684, filed Oct. 12, 2011 and published as US 2012-0046178 on Feb. 23, 2012.
Office Action dated Feb. 7, 2019 in U.S. Appl. No. 13/790,996, filed Mar. 8, 2013 and published as US 2014-0011195 on Jan. 9, 2014.
Office Action dated Mar. 8, 2019 in U.S. Appl. No. 13/551,486, filed Jul. 17, 2012 and published as US 2013-0017960 on Jan. 17, 2013.
Singer-Sam et al., "A Sensitive, Quantitative Assay for Measurement of Allele-specific Transcripts Differing by a Single Nucleotide" Genome Research (1992) 1:160-163.

(Continued)

*Primary Examiner* — James Martinell
(74) *Attorney, Agent, or Firm* — Grant IP, Inc.

(57) ABSTRACT

Provided herein are multiplex methods for detecting the presence or absence and amount of variants of a plurality of target nucleic acid species having low-abundance variants and high-abundance variants.

20 Claims, 1 Drawing Sheet

(56) References Cited

U.S. PATENT DOCUMENTS

| | | |
|---|---|---|
| 6,235,478 B1 | 5/2001 | Koster |
| 6,238,871 B1 | 5/2001 | Koster |
| 6,258,538 B1 | 7/2001 | Koster et al. |
| 6,268,144 B1 | 7/2001 | Koster et al. |
| 6,277,573 B1 | 8/2001 | Koster |
| 6,300,076 B1 | 10/2001 | Koster |
| 6,428,955 B1 | 8/2002 | Koster et al. |
| 6,500,621 B2 | 12/2002 | Koster |
| 6,602,662 B1 | 8/2003 | Koster et al. |
| 6,613,509 B1 | 9/2003 | Chen |
| 7,074,563 B2 | 7/2006 | Koster |
| 7,108,974 B2 | 9/2006 | Ecker et al. |
| 7,198,893 B1 | 4/2007 | Koster et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 7,419,787 B2 | 9/2008 | Koster |
| 7,759,065 B2 | 7/2010 | Koster |
| 8,003,317 B2 | 8/2011 | Beaulieu et al. |
| 8,349,566 B2 | 1/2013 | Beaulieu et al. |
| 8,586,708 B2 | 11/2013 | Ting et al. |
| 2003/0022225 A1 | 1/2003 | Monforte et al. |
| 2003/0119004 A1 | 6/2003 | Wenz et al. |
| 2003/0203381 A1 | 10/2003 | Kambara et al. |
| 2004/0259105 A1 | 12/2004 | Fan et al. |
| 2005/0079521 A1 | 4/2005 | Beaulieu et al. |
| 2005/0287533 A1 | 12/2005 | Ehrich et al. |
| 2005/0287592 A1 | 12/2005 | Kless |
| 2006/0003352 A1 | 1/2006 | Lipkin et al. |
| 2006/0166201 A1 | 7/2006 | Schatz et al. |
| 2007/0202514 A1 | 8/2007 | Koster et al. |
| 2007/0292861 A1 | 12/2007 | Thompson |
| 2008/0167197 A1 | 7/2008 | Schmidt et al. |
| 2008/0305479 A1 | 12/2008 | Van Den Boom |
| 2011/0165133 A1 | 7/2011 | Rabinovich et al. |
| 2012/0015826 A1 | 1/2012 | Beaulieu et al. |
| 2012/0156685 A1 | 6/2012 | Cantor et al. |
| 2013/0017960 A1 | 1/2013 | Honisch et al. |
| 2013/0237428 A1 | 9/2013 | Beaulieu et al. |
| 2016/0102347 A1 | 4/2016 | Beaulieu et al. |
| 2016/0312278 A1 | 10/2016 | Nygren |
| 2019/0153526 A1 | 5/2019 | Nygren |

FOREIGN PATENT DOCUMENTS

| | | |
|---|---|---|
| EP | 0655501 | 5/1995 |
| EP | 1 176 212 | 1/2002 |
| JP | 7-159404 | 6/1995 |
| JP | 8-256764 | 10/1996 |
| JP | 11-501008 | 1/1999 |
| JP | 2004-527732 | 9/2004 |
| JP | 2005-336107 | 12/2005 |
| JP | 2006-320271 | 11/2006 |
| JP | 2008-531052 | 8/2008 |
| WO | WO 89/10977 | 11/1989 |
| WO | WO 91/011533 | 8/1991 |
| WO | WO 92/013969 | 8/1992 |
| WO | WO 94/000562 | 1/1994 |
| WO | WO 94/016101 | 7/1994 |
| WO | WO 96/030545 | 10/1996 |
| WO | WO 96/032504 | 10/1996 |
| WO | WO 97/037041 | 10/1997 |
| WO | WO 04/007773 | 1/2004 |
| WO | WO 05/012578 | 2/2005 |
| WO | WO 10/056513 | 5/2010 |
| WO | WO 11/034115 | 3/2011 |
| WO | WO 12/159089 | 11/2012 |
| WO | WO 16/172571 | 10/2016 |
| WO | WO 16/172579 | 10/2016 |

OTHER PUBLICATIONS

Yao et al., "Purification and characterization of a novel deoxyinosine-specific enzyme, deoxyinosine 3' endonuclease, from *Escherichia coli*" Journal of Biological Chemistry (1994) 269:16260-16268.

Yao and Kow, "Interaction of deoxyinosine 3'-endonuclease from *Escherichia coli* with DNA containing deoxyinosine" Journal of Biological Chemistry (1995) 270:28609-28616.

Yao and Kow, "Strand-specific cleavage of mismatch-containing DNA by deoxyinosine 3'-endonuclease from *Escherichia coli*" Journal of Biological Chemistry (1994) 269:31390-31396.

Office Action dated May 13, 2019 in U.S. Appl. No. 16/255,718, filed Jan. 23, 2019 and published as US 2019-0153526 on May 23, 2019.

Adler et al. "Cell Membrane Coating with Glutaraldehyde: Application to a versatile Solid-Phase Assay for Thyroid Membrane Proteins and Molecules Interacting with Thyroid Membranes," Analytical Chemistry 148:320-327 (1985).

Anker et al., Hum. Mol. Genet. 1:137 (1992).

Banerjee et al., Science 263:227 (1994).

Beckmann et al., Genomics (1992) 12:627-631.

Binladen et al., "The use of coded PCR primers enables high-throughput sequencing of multiple homolog amplification products by 454 parallel sequencing" Plos One (2007) 2(2):e197:1-9.

Bird, Genes Dev., 16:6-21 (2002).

Caruthers C.H., "Gene synthesis machines: DNA chemistry and its uses", Science, 230:281-285 (1985).

Caruthers et al., "Chemical synthesis of deoxyoligonucleotides by the phosphoramidite method", in Methods in Enzymology 154:287-313 (1987).

Caskey et al., Science 256, 784 (1992).

Chakrabarti et al., Nature, 328:534-547 (1987).

Chee, Enzymatic multiples DNA sequencing, Nucleic Acids Res. 19(12): 3301-3305 (1991).

Cook et al., "Synthesis and hybridization of a series of biotinylated oligonucleotides", Nucleic Acids Research 16:4077-4095 (1988).

Ding et al., "MS analysis of single-nucleotide differences in circulating nucleic acids: Application to noninvasive prenatal diagnosis" PNAS USA (2004) 101(29):10762-10767.

Doktycz et al., "Analysis of Polymerase Chain Reaction-Amplified DNA Products by Mass Spectrometry Using Matrix Assisted Laser Desorption and Electrospray: Current Status" Anal. Biochem. 230: 205-214 (1995).

Dubiley et al., "Polymorphism analysis and gene detection by minisequencing on an array of gel-immobilized primers" Nucleic Acids Research (1999) 27(18):1-6 e19.

Duffield et al., "Simultaneous determination of multiple mRNA levels utilizing MALDI-TOF mass spectrometry and biotinylated dideoxynucleotides" RNA (2010) 16:1285-1291.

Eckstein, F., (Ed.) Oligonucleotides and Analogues: A Practical Approach Oxford:Oxford University Press, 56-57, 137-139, 256-259, (1991).

Edwards et al., Nucl Acids Res. 19:4791 (1991).

Fan et al., "Parallel genotyping of human SNPs using generic high-density oligonucleotide tag arrays" Genome Research (2000) 10(6):853-860.

Fitzgrald et al., "Basic Matrices for the Matrix-Assisted Laser Desorption/Ionization Mass Spectrometry of Proteins and Oligonucleotides", Anal. Chem., 65:3204-3211 (1993).

Ganem et al., Detection of oligonucleotide duplex forms by ion-spray mass spectrometry, Tetrahedron Letters 34(9): 1445-1448 (1993).

Gardner et al., "Acyclic and dideoxy terminator preferences denote divergent sugar recognition by archaeon and Taq DNA polymerases" Nucleic Acids Research (2002) 30(2):605-613.

German et al., Clin. Genet. 35:57 (1989).

Gust et al., Intervirology, 20:1-7 (1983).

Guyader et al., Nature 328:662-669 (1987).

Haff et al., "Single-nucleotide polymorphism identification assays using a thermostable DNA polymerase and delayed extraction MALDI-TOF mass spectrometry" Genome Research (1997) 7:378-388.

Hartmer et al., "RNase T1 mediated base-specific cleavage and MALDI-TOF MS for high-throughput comparative sequence analysis" Nucleic Acids Research (2003) 31(9):e47:1-10.

Heym et al., Lancet 344:293 (1994).

(56) References Cited

OTHER PUBLICATIONS

Hirsch et al., "Easily reversible desthiobiotin binding to streptavidin, avidin, and other biotin-binding proteins: uses for protein labeling, detection and isolation" Analytical Biochemistry (2002) 308:343-357.
Hirschhorn et al., "SBE-TAGS: An array-based method for efficient single-nucleotide polymorphism genotyping". PNAS. US. vo 1. 97. No. 22. Oct. 24, 2000 (Oct. 24, 2000). pp. 12164-12169.
Hitchcock et al., "Cleavage of deoxyoxanosine-containing oligodeoxyribonucleotides by bacterial endonuclease V" Nucleic Acids Research (2004) 32(13):4071-4080.
Holmberg et al., "The biotin-streptavidin interaction can be reversibly broken using water at elevated temperatures" Electrophoresis (2005) 26:501-510.
Jacobson et al., Applications of Mass Spectrometry to DNA Sequencing, Genet. Anal. Tech. Appl. 8(8): 223-229 (1991).
Jeffreys et al., Nature 314:67-73 (1985).
Khrapko et al., "A method for DNA sequencing by hybridization with oligonucleotide matrix," J. DNA Sequencing and Mapping 1: 375-388 (1991).
Kim et al., "Digital genotyping using molecular affinity and mass spectrometry" Nature Review Genetics (2003) 4:1001-1008.
Kim et al., "Multiples genotyping of the human beta 2-adrenergic receptor gene using solid-phase captureable dideoxynucleotides and mass spectrometry" Analytical Biochemistry (2003) 316:251-258.
Lai-Qiang Ying et al., Chemical Communications (2011) 47:8593-8595.
Lefmann et al., "Novel mass spectrometry-based tool for genotypic identification of mycobacteria" Jounrnal of Clinical Microbiology (2004) 42:339-346.
Leonard et al., "High-resolution structure of a mutagenic lesion in DNA," Proc. Natl. Acad. Sci. USA 87: 9573-9576 (1990).
Litt et al., Nucleic Acids Res. 18:4301 (1990).
Litt et al., Nucleic Acids Res. 18:5921 (1990).
Luty et al., Am. J. Hum. Genet. 46:776-783 (1990).
Luty et al., Nucleic Acids Res. 19:4308 (1991).
Matthews et al., "Analytical Strategies for the Use of DNA Probes," Analytical Biochemistry 169: 1-25 (1988).
Mckinnon, "Ataxia-telangiectasia: an inherited disorder of ionizing-radiation sensitivity in man. Progress in the elucidation of the underlying biochemical defect" Hum. Genet. (1987) 75(3):197-208.
Mizusawa et al., Improvement of the Dideoxy Chain Termination Method of DNA Sequencing by use of Deoxy-7-Deazaguanosine Triphosphate in Place of dGTP, Nucleic Acids Research, vol. 14, No. 3, pp. 1319-1325 (1986).
Morris et al., J. Infect. Dis. 171:954 (1995).
Morrison et al. (Eds.), in Organic Chemistry, published by Allyn and Bacon, Inc., Boston, Massachusetts, USA, pp. 406-409 (1973).
Muddiman et al., Anal. Chem. (1997) 69:1543-1549.
Naito et al., "Molecular Mass Measurement of Polymerase Chain Reaction Products Amplified from Human Blood DNA by Electrospray Ionization Mass Spectrometry," Rapid Communications in Mass Spectrometry, vol. 9, 1484-1486 (1995).
Nakamura et al., Science 235:1616-1622 (1987).
Hammond et al., "Rapid mass spectrometric identification of human genomic polymorphisms using multiplexed photocleavable mass-tagged probes and solid phase capture" Organic and Biomolecular Chemistry (2007) 5(12):1878-1895.
Nishimura et al., Nucl. Acids Res. 20:1167 (1992).
Nordhoff et al., "Matrix-assisted laser desorption/ionization mass spectrometry of nucleic acids with wavelengths in the ultraviolet and infrared", Rapid Commun Mass Spectrom. Dec. 1992;6(12):771-776.
Oeth et al., SEQUENOM® Application Note, Document No. 8876-006, R04, published Nov. 10, 2006.
Overberg et al., "Matrix-assisted laser desorption of large biomolecules with a TEA-CO.sub.2-laser", Rapid Comm in Mass Spectro 5(3):128-131 (1991).
Palejwala et al., Quantitative Multiplex Sequence Analysis of Mutational Hot Spots. Frequency and Specificity of Mutations Induced by a Site-Specific Ethenocytosine in M13 Viral DNA, Biochemistry 32: 4105-4111 (1993).
Pieles et al., Matrix-assisted laser desorption ionization time-of-flight mass spectrometry: a powerful tool for the mass and sequence analysis of natural and modified oligonucleotides, Nucleic Acids Res. 21(14): 3191-3196 (1993).
Pierce et al., J.Clin. Microbiol. (2012) 50(11):3458-3465.
Ploos et al., Nucl Acids Res. 18:4957(1990).
Polymeropoulos et al., Nucl. Acids Res. 18:7468 (1990).
Polymeropoulos et al., Nucl. Acids Res. 19:195 (1991).
Polymeropoulos et al., Nucl. Acids Res. 19:4018 (1991).
Polymeropoulos et al., Nucl. Acids Res. 19:4306 (1991).
Ratner et al., Nature, 313:227-284 (1985).
Reymer et al., Nature Genetics 10:28-34 (1995).
Rosli et al., "Quantitative recovery of biotinylated proteins from streptavidin-based affinity chromatography resins" Methods Mol. Biol. (2008) 418:89-100.
Rybak et al., "Purification of biotinylated proteins on streptavidin resin: a protocol for quantitative elution" Proteomics (2004) 4:2296-2299.
Sano and Cantor, "Intersubunit contacts made by tryptophan 120 with biotin are essential for both strong biotin binding and biotin-induced tighter subunit association of streptavidin" PNAS USA (1995) 92:3180-3184.
Schechter et al., Nature Genetics (1994) 6:29-32.
Schlesinger, D. H ., Macromolecular Sequencing and Synthesis: Selected Methods and Applications, Alan R. Liss, Inc., New York, (1988), Title and copyright pages only.
Stahl et al., Solid Phase DNA Sequencing using the Biotin-Avidin System, Nucleic Acids Research 16(7): 3025-3039 (1988).
Stanssens et al., "High-throughput MALDI-TOF discovery of genomic sequence polymorphisms" Genome Research (2004) 14:126-133.
Takenaka et al., "Multiplex single-base extension typing to identify nuclear genes required for RNA editing plant organelles" Nucleic Acids Research (2008) 37(2):e13.
Tautz, Nucl Acids Res. 17:6463-6471 (1989).
Thompson et al., "Electrospray ionization-cleavable tandem nucleic acid mass tag-peptide nucleic acid conjugates: synthesis and applications to quantitative genomic analysis using electrospray ionisation-MS/MS" Nucleic Acids Research (2007) 35(4):e28 1-13.
Tost et al., "Genotyping Single Nucleotide Polymorphisms by Mass Spectrometry" Mass Spectrometry Reviews (2002) 21:388-418.
Trainor, DNA Sequencing, Automation and the Human Genome, Anal. Chem. 62: 418-426 (1990).
Tsang et al., "Mass spectrometry-based detection of hemoglobin E mutation by allele-specific base extension reaction" Clin. Chem. (2007) 53(12):2205-2209.
Tuschihashi et al., "Progress in high throughput SNP genotyping methods" Pharmacogenomics Journal (2002) 2:103-110.
Uhlmann et al., "Antisense Oligonucleotides: A New Therapeutic Principle," Chemical Reviews 90(4): 544-583 (1990).
Vivante et al., "High-throughput, sensitive and quantitative assay for the detection of BCR-ABL kinase domain mutations" Leukemia (2007) 21:1318-1321.
Wain Hobson et al., Cell, 40:9-17 (1985).
Wang et al., Science (1998) 280: 1077-1082.
Weber et al., Am. J. Hum. Genet. 44:388 (1989).
Weissenbach et al., Nature 358, 794 (1992).
Wu et al., Matrix-assisted Laser Desorption Time-of-flight Mass Spectrometry of Oligonucleotides Using 3-Hydroxypicolinic Acid as an Ultraviolet-sensitive Matrix, Rapid Comm Mass Spec 7: 142-146 (1993).
Wunschel et al., "Analysis of Double-stranded Polymerase Chain Reaction Products from he Bacillus cereus Group by Electrospray Ionization Fourier Transform Ion Cyclotron Resonance Mass Spectrometry," Rapid Communications in Mass Spectrometry, vol. 10, 29-35 (1996).
Yolov et al., Synthesis of RNA using T7 RNA polymerase and immobilized DNA in a stream type reactor, Biooraanicheskala Khhimia, 17(6) 789-794 (1991) With English Translation.
Zuliani et al., Nucl. Acids Res. 18:4958 (1990).

(56) References Cited

OTHER PUBLICATIONS

International Preliminary Report on Patentability dated Oct. 24, 2017 in International Application No. PCT/US2016/028971 filed: Apr. 22, 2016 and published as: WO/2016/172571 on: Oct. 27, 2016.
International Search Report and Written Opinion dated Jul. 15, 2016 in International Application No. PCT/US2016/028971 filed: Apr. 22, 2016 and published as: WO/2016/172571 on: Oct. 27, 2016.
International Preliminary Report on Patentability dated Nov. 2, 2017 in International Application No. PCT/US2016/028980 filed: Apr. 22, 2016 and published as: WO2016172579 on: Nov. 27, 2016.
International Search Report and Written Opinion dated Jun. 22, 2016 in International Application No. PCT/US2016/028980 filed: Apr. 22, 2016 and published as: WO2016172579 on: Nov. 27, 2016.
Non-Final Office Action dated May 29, 2018 in U.S. Appl. No. 15/136,024, filed Apr. 22, 2016 and published as: US 2016/0312278 on: Oct. 27, 2016.
Extended European Search Report dated Oct. 15, 2012 from EP Application No. EP 09826542.4-2402, published as EP 2 356 259.
International Preliminary Report on Patentability dated May 3, 2011 in International Patent Application No. PCT/US2009/062239 filed on Oct. 27, 2009 and published as WO 10/056513 on May 20, 2010.
International Search Report and Written Opinion dated Jul. 9, 2010 in International Patent Application No. PCT/US2009/062239 filed on Oct. 27, 2009 and published as WO 10/056513 on May 20, 2010.
International Preliminary Report on Patentability dated Nov. 28, 2013 in International Application No. PCT/US2012/038710, filed on May 18, 2012 and published as WO 2012/159089 on Nov. 22, 2012.
International Search Report and Written Opinion dated Sep. 5, 2012 in International Patent Application no. PCT/US2012/038710 filed on May 18, 2012 and published as WO 2012/159089 on Nov. 22, 2012.
Office Action dated Jan. 17, 2018 in U.S. Appl. No. 13/790,996, filed Mar. 8, 2013 and published as US 2014-0011195 on Jan. 9, 2014.
Office Action dated Jun. 27, 2017 in U.S. Appl. No. 13/790,996, filed Mar. 8, 2013 and published as US 2014-0011195 on Jan. 9, 2014.
Office Action dated Dec. 16, 2016 in U.S. Appl. No. 13/790,996, filed Mar. 8, 2013 and published as US 2014-0011195 on Jan. 9, 2014.
Office Action dated Apr. 22, 2016 in U.S. Appl. No. 13/790,996, filed Mar. 8, 2013 and published as US 2014-0011195 on Jan. 9, 2014.
Office Action dated Jan. 6, 2016 in U.S. Appl. No. 13/790,996, filed on Mar. 8, 2013 and published as US 2014-0011195 on Jan. 9, 2014.
Office Action dated Jun. 19, 2015 in U.S. Appl. No. 13/790,996, filed Mar. 8, 2013 and published as US 2014-0011195 on Jan. 9, 2014.
Office Action dated Oct. 3, 2014 in U.S. Appl. No. 13/790,996, filed Mar. 8, 2013 and published as US 2014-0011195 on Jan. 9, 2014.
Office Action dated Jun. 28, 2018 in U.S. Appl. No. 13/126,684, filed Oct. 12, 2011 and published as US 2012-0046178 on Feb. 23, 2012.
Office Action dated Nov. 15, 2017 in U.S. Appl. No. 13/126,684, filed Oct. 12, 2011 and published as US 2012-0046178 on Feb. 23, 2012.
Office Action dated Jul. 18, 2017 in U.S. Appl. No. 13/126,684, filed Oct. 12, 2011 and published as US 2012-0046178 on Feb. 23, 2012.
Office Action dated Jan. 17, 2017 in U.S. Appl. No. 13/126,684, filed Oct. 12, 2011 and published as US 2012-0046178 on Feb. 23, 2012.
Office Action dated Oct. 3, 2016 in U.S. Appl. No. 13/126,684, filed Oct. 12, 2011 and published as US 2012-0046178 on Feb. 23, 2012.
Office Action dated Jan. 29, 2016 in U.S. Appl. No. 13/126,684, filed Oct. 12, 2011 and published as US 2012-0046178 on Feb. 23, 2012.
Office Action dated Dec. 26, 2014 in U.S. Appl. No. 13/126,684, filed Oct. 12, 2011 and published as US 2012-0046178 on Feb. 23, 2012.
Office Action dated Apr. 10, 2014 in U.S. Appl. No. 13/126,684, filed Oct. 12, 2011 and published as US 2012-0046178 on Feb. 23, 2012.
Office Action dated Aug. 3, 2018 in U.S. Appl. No. 13/551,486, filed Jul. 17, 2012 and published as US 2013-0017960 on Jan. 17, 2013.
Office Action dated Jan. 9, 2018 in U.S. Appl. No. 13/551,486, filed Jul. 17, 2012 and published as US 2013-0017960 on Jan. 17, 2013.
Office Action dated Jun. 15, 2017 in U.S. Appl. No. 13/551,486, filed Jul. 17, 2012 and published as US 2013-0017960 on Jan. 17, 2013.
Office Action dated Jan. 20, 2017 in U.S. Appl. No. 13/551,486, filed Jul. 17, 2012 and published as US 2013-0017960 on Jan. 17, 2013.
Office Action dated Oct. 4, 2016 in U.S. Appl. No. 13/551,486, filed Jul. 17, 2012 and published as US 2013-0017960 on Jan. 17, 2013.
Office Action dated Dec. 30, 2015 in U.S. Appl. No. 13/551,486, filed Jul. 17, 2012 and published as US 2013-0017960 on Jan. 17, 2013.
Office Action dated Jul. 8, 2015 in U.S. Appl. No. 13/551,486, filed Jul. 17, 2012 and published as US 2013-0017960 on Jan. 17, 2013.
Office Action dated Feb. 26, 2014 in U.S. Appl. No. 13/551,486, filed Jul. 17, 2012 and published as US 2013-0017960 on Jan. 17, 2013.
Office Action dated Sep. 5, 2013 in U.S. Appl. No. 13/551,486, filed Jul. 17, 2012 and published as US 2013-0017960 on Jan. 17, 2013.
Office Action dated Feb. 28, 2013 in U.S. Appl. No. 13/551,486, filed Jul. 17, 2012 and published as US 2013-0017960 on Jan. 17, 2013.
Office Action dated Jun. 29, 1993 in U.S. Appl. No. 08/001,323, filed Jan. 7, 1993, Abandoned.
Office Action dated Apr. 5, 1994 in U.S. Appl. No. 08/001,323, filed Jan. 7, 1993, Abandoned.
Office Action dated Feb. 23, 1995 in U.S. Appl. No. 08/178,216, filed Jan. 6, 1994, now U.S. Pat. No. 5,547,835 issued on Aug. 20, 1996.
Office Action dated Aug. 22, 1995 in U.S. Appl. No. 08/178,216, filed Jan. 6, 1994, now U.S. Pat. No. 5,547,835 issued on Aug. 20, 1996.
Office Action dated Apr. 15, 1996 in U.S. Appl. No. 08/406,199, filed Mar. 17, 1995 now U.S. Pat. No. 5,605,798 issued on Feb. 25, 1997.
Office Action dated Sep. 14, 1995 in U.S. Appl. No. 08/406,199, filed Mar. 17, 1995 now U.S. Pat. No. 5,605,798 issued on Feb. 25, 1997.
Office Action dated Nov. 6, 1997 in U.S. Appl. No. 08/617,256, filed Mar. 18, 1996 now U.S. Pat. No. 6,043,031 issued on Mar. 28, 2000.
Office Action dated Sep. 10, 1999 in U.S. Appl. No. 08/617,256, filed Mar. 18, 1996 now U.S. Pat. No. 6,043,031 issued on Mar. 28, 2000.
Office Action dated May 5, 1997 in U.S. Appl. No. 08/617,256, filed Mar. 18, 1996 now U.S. Pat. No. 6,043,031 issued on Mar. 28, 2000.
Office Action dated Feb. 3, 1998 in U.S. Appl. No. 08/617,256, filed Mar. 18, 1996 now U.S. Pat. No. 6,043,031 issued on Mar. 28, 2000.
Office Action dated Oct. 21, 1998 in U.S. Appl. No. 08/617,256, filed Mar. 18, 1996 now U.S. Pat. No. 6,043,031 issued on Mar. 28, 2000.
Office Action dated Apr. 20, 1999 in U.S. Appl. No. 08/617,256, filed Mar. 18, 1996 now U.S. Pat. No. 6,043,031 issued on Mar. 28, 2000.
Office Action dated Feb. 16, 2000 in U.S. Appl. No. 09/287,141, filed Apr. 6, 1999 now U.S. Pat. No. 6,197,489 issued on Mar. 6, 2001.
Office Action dated May 30, 2000 in U.S. Appl. No. 09/287,141, filed Apr. 6, 1999 now U.S. Pat. No. 6,197,489 issued on Mar. 6, 2001.
Office Action dated Feb. 16, 2000 in U.S. Appl. No. 09/287,682, filed Apr. 6, 1999 now U.S. Pat. No. 6,235,478 issued on May 22, 2001.

(56) References Cited

OTHER PUBLICATIONS

Office Action dated Jun. 14, 2000 in U.S. Appl. No. 09/287,682, filed Apr. 6, 1999 now U.S. Pat. No. 6,235,478 issued on May 22, 2001.
Office Action dated May 5, 2000 in U.S. Appl. No. 09/287,679, filed Apr. 6, 1999 now U.S. Pat. No. 6,258,538 issued on Jul. 10, 2001.
Office Action dated Sep. 22, 2000 in U.S. Appl. No. 09/287,679, filed Apr. 6, 1999 now U.S. Pat. No. 6,258,538 issued on Jul. 10, 2001.
Office Action dated Nov. 16, 2000 in U.S. Appl. No. 09/287,679, filed Apr. 6, 1999 now U.S. Pat. No. 6,258,538 issued on Jul. 10, 2001.
Office Action dated Feb. 25, 2000 in U.S. Appl. No. 09/287,681, filed Apr. 6, 1999 now U.S. Pat. No. 6,277,573 issued on Aug. 21, 2001.
Office Action dated Jun. 28, 2000 in U.S. Appl. No. 09/287,681, filed Apr. 6, 1999 now U.S. Pat. No. 6,277,573 issued on Aug. 21, 2001.
Office Action dated Aug. 21, 2000 in U.S. Appl. No. 09/431,613, filed Nov. 2, 1999 now U.S. Pat. No. 6,221,601 issued on Apr. 24, 2001.
Office Action dated Oct. 10, 2000 in U.S. Appl. No. 09/431,613, filed Nov. 2, 1999 now U.S. Pat. No. 6,221,601 issued on Apr. 24, 2001.
Office Action dated Sep. 8, 2000 in U.S. Appl. No. 09/495,444, filed Jan. 31, 2000 now U.S. Pat. No. 6,300,076 issued on Oct. 9, 2001.
Office Action dated Nov. 3, 2000 in U.S. Appl. No. 09/495,444, filed Jan. 31, 2000 now U.S. Pat. No. 6,300,076 issued on Oct. 9, 2001.
Office Action dated Sep. 8, 2000 in U.S. Appl. No. 09/397,766, filed Sep. 15, 1999 now U.S. Pat. No. 6,268,144 issued on Jul. 31, 2001.
Office Action dated Sep. 8, 2000 in U.S. Appl. No. 09/504,245, filed Feb. 15, 2000 now U.S. Pat. No. 6,221,605 issued on Apr. 24, 2001.
Office Action dated Oct. 20, 2000 in U.S. Appl. No. 09/504,245, filed Feb. 15, 2000 now U.S. Pat. No. 6,221,605 issued on Apr. 24, 2001.
Office Action dated Jun. 28, 2002 in U.S. Appl. No. 09/724,877, filed Nov. 28, 2000 now U.S. Pat. No. 6,602,662 issued on Aug. 5, 2003.
Office Action dated Sep. 19, 2002 in U.S. Appl. No. 09/724,877, filed Nov. 28, 2000 now U.S. Pat. No. 6,602,662 issued on Aug. 5, 2003.
Office Action dated Dec. 19, 2001 in U.S. Appl. No. 09/796,416, filed Feb. 28, 2001 now U.S. Pat. No. 6,500,621 issued on Dec. 31, 2002.
Office Action dated May 17, 2002 in U.S. Appl. No. 09/796,416 filed Feb. 28, 2001 now U.S. Pat. No. 6,500,621 issued on Dec. 31, 2002.
Office Action dated Apr. 10, 2002 in U.S. Appl. No. 09/879,341, filed Jun. 11, 2001 now U.S. Pat. No. 6,589,485 issued on Jul. 8, 2003.
Office Action dated Nov. 27, 2002 in U.S. Appl. No. 09/879,341, filed Jun. 11, 2001 now U.S. Pat. No. 6,589,485 issued on Jul. 8, 2003.
Office Action dated Aug. 5, 2005 in U.S. Appl. No. 10/375,714, filed Feb. 24, 2003 now U.S. Pat. No. 7,074,563 issued on Jul. 11, 2006.
Office Action dated Jan. 10, 2006 in U.S. Appl. No. 10/375,714, filed Feb. 24, 2003 now U.S. Pat. No. 7,074,563 issued on Jul. 11, 2006.
Office Action dated Jul. 3, 2007 in U.S. Appl. No. 11/432,171, filed May 11, 2006 now U.S. Pat. No. 7,419,787 issued on Sep. 2, 2008.
Office Action dated Feb. 25, 2008 in U.S. Appl. No. 11/432,171, filed May 11, 2006 now U.S. Pat. No. 7,419,787 issued on Sep. 2, 2008.
Office Action dated Feb. 23, 2010 in U.S. Appl. No. 12/125,857, filed May 22, 2008 published as.: US-2009/0092977 published on Apr. 9, 2009 and now U.S. Pat. No. 7,759,065 on May 20, 2010.
Office Action dated May 11, 2009 in U.S. Appl. No. 12/125,857, filed May 22, 2008 published as.: US-2009/0092977 published on Apr. 9, 2009 and now U.S. Pat. No. 7,759,065 on May 20, 2010.

Office Action dated May 20, 2009 in U.S. Appl. No. 12/163,915, filed Jun. 27, 2008 published as.: US-2009/0042203 published on Feb. 12, 2009.
Office Action dated Nov. 3, 2010 in U.S. Appl. No. 12/795,155, filed Jun. 7, 2010 published as.: US-2011/0027773 published on Feb. 3, 2011.
Office Action dated Sep. 8, 2014 in U.S. Appl. No. 13/099,236, filed May 2, 2011 and published as US 2011-0269643 on Nov. 3, 2011.
Office Action dated Aug. 17, 1998 in U.S. Appl. No. 08/744,481, filed Nov. 6, 1996 now U.S. Pat. No. 6,428,955 issued on Aug. 6, 2002.
Office Action dated Apr. 1, 1999 in U.S. Appl. No. 08/744,481, filed Nov. 6, 1996 now U.S. Pat. No. 6,428,955 issued on Aug. 6, 2002.
Office Action dated Jan. 2, 2001 in U.S. Appl. No. 08/744,481, filed Nov. 6, 1996 now U.S. Pat. No. 6,428,955 issued on Aug. 6, 2002.
Office Action dated Jul. 6, 2000 in U.S. Appl. No. 09/179,536, filed Oct. 26, 1998 published as.: US-2002/0042112 published on Apr. 11, 2002.
Office Action dated Mar. 28, 2001 in U.S. Appl. No. 09/179,536, filed Oct. 26, 1998 published as.: US-2002/0042112 published on Apr. 11, 2002.
Office Action dated Dec. 26, 2001 in U.S. Appl. No. 09/179,536, filed Oct. 26, 1998 published as.: US-2002/0042112 published on Apr. 11, 2002.
Office Action dated Jul. 25, 2002 in U.S. Appl. No. 09/179,536, filed Oct. 26, 1998 published as.: US-2002/0042112 published on Apr. 11, 2002.
Office Action dated Aug. 8, 2001 in U.S. Appl. No. 09/297,576, filed Jun. 28, 1999 published as.: US-2003/129589 published on Jul. 10, 2003.
Office Action dated May 8, 2002 in U.S. Appl. No. 09/297,576, filed Jun. 28, 1999 published as.: US-2003/-129589 published on Jul. 10, 2003.
Office Action dated Nov. 20, 2002 in U.S. Appl. No. 09/686,148, filed Oct. 10, 2000 now U.S. Pat. No. 7,198,893 issued on Apr. 3, 2007.
Office Action dated Aug. 27, 2003 in U.S. Appl. No. 09/686,148, filed Oct. 10, 2000 now U.S. Pat. No. 7,198,893 issued on Apr. 3, 2007.
Office Action dated Apr. 19, 2005 in U.S. Appl. No. 09/686,148, filed Oct. 10, 2000 now U.S. Pat. No. 7,198,893 issued on Apr. 3, 2007.
Office Action dated Apr. 28, 2006 in U.S. Appl. No. 09/686,148, filed Oct. 10, 2000 now U.S. Pat. No. 7,198,893 issued on Apr. 3, 2007.
Office Action dated May 8, 2002 in U.S. Appl. No. 09/783,881, filed Feb. 13, 2001 now abandonded.
Office Action dated Aug. 27, 2002 in U.S. Appl. No. 09/783,881, filed Feb. 13, 2001 now abandonded.
Office Action dated Feb. 20, 2008 in U.S. Appl. No. 11/541,871, filed Oct. 2, 2006 now U.S. Pat. No. 7,501,251 issued on Mar. 10, 2009.
Office Action dated Oct. 8, 2008 in U.S. Appl. No. 11/541,871, filed Oct. 2, 2006 now U.S. Pat. No. 7,501,251 issued on Mar. 10, 2009.
Office Action dated Nov. 16, 2009 in U.S. Appl. No. 12/163,923, filed Jun. 27, 2008 and published as: US-2009-0023150 on Jan. 22, 2009.
Office Action dated Feb. 6, 2009 in U.S. Appl. No. 12/163,923, filed Jun. 27, 2008 and published as: US-2009-0023150 on Jan. 22, 2009.
Office Action dated Mar. 20, 1997 in U.S. Appl. No. 08/467,208, filed Jun. 6, 1995 now abandoned.
Office Action dated Oct. 28, 1997 in U.S. Appl. No. 08/467,208, filed Jun. 6, 1995 now abandoned.
Office Action dated Aug. 19, 1998 in U.S. Appl. No. 08/467,208, filed Jun. 6, 1995 now abandoned.
Office Action dated Jan. 12, 1999 in U.S. Appl. No. 08/467,208, filed Jun. 6, 1995 now abandoned.
Office Action dated Oct. 13, 1999 in U.S. Appl. No. 08/467,208, filed Jun. 6, 1995 now abandoned.
Office Action dated Jul. 31, 2000 in U.S. Appl. No. 08/467,208, filed Jun. 6, 1995 now abandoned.
Office Action dated Mar. 26, 2001 in U.S. Appl. No. 08/467,208, filed Jun. 6, 1995 now abandoned.

(56) References Cited

OTHER PUBLICATIONS

Office Action dated Jul. 16, 2001 in U.S. Appl. No. 08/467,208, filed Jun. 6, 1995 now abandoned.
Office Action dated Jul. 29, 2002 in U.S. Appl. No. 08/467,208, filed Jun. 6, 1995 now abandoned.
Office Action dated Aug. 1, 2003 in U.S. Appl. No. 08/467,208, filed Jun. 6, 1995 now abandoned.
Office Action dated Sep. 9, 2004 in U.S. Appl. No. 08/467,208, filed Jun. 6, 1995 now abandoned.
Office Action dated Sep. 8, 2005 in U.S. Appl. No. 08/467,208, filed Jun. 6, 1995 now abandoned.
Nguyen et al., "Mild conditions for releasing mono and bis-biotinylated macromolecules from immobilized streptavidin" Biomolecular Engineering (2005) 22:147-150.
Mosko et al., "Ultrasensitive Detection of Multiplexed Somatic Mutations Using MALDI-TOF Mass Spectrometry" The Journal of Molecular Diagnostics (2016) 18:23-31.
Office Action dated Aug. 2, 2019 in U.S. Appl. No. 16/255,718, filed Jan. 23, 2019 and published as US 2019-0153526 on May 23, 2019.
Office Action dated Aug. 22, 2019 in U.S. Appl. No. 13/126,684, filed Oct. 12, 2011 and published as US 2012-0046178 on Feb. 23, 2012.

\* cited by examiner

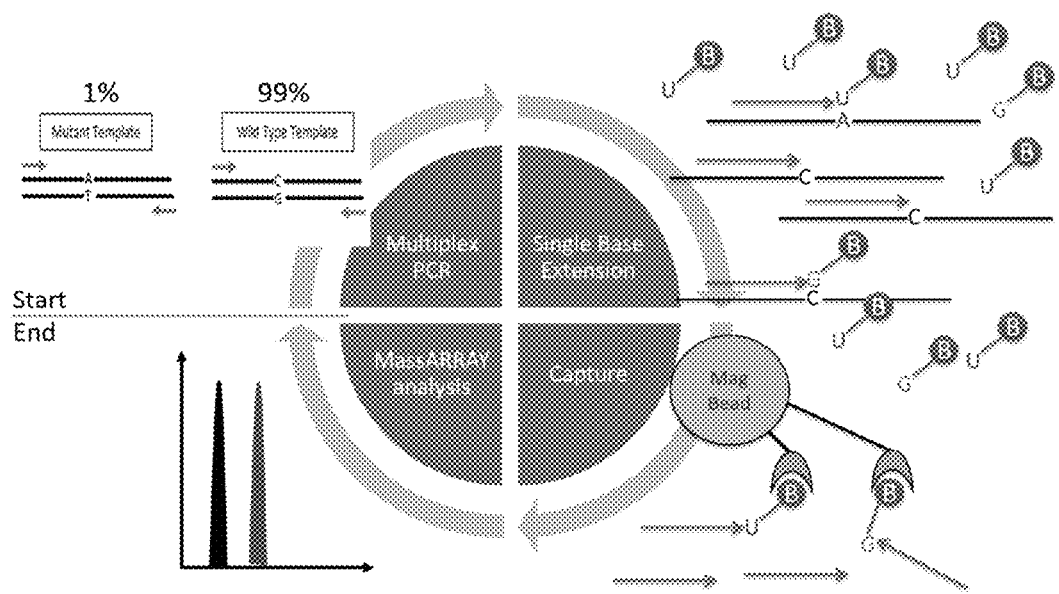

MULTIPLEX METHODS FOR DETECTION AND QUANTIFICATION OF MINOR VARIANTS

RELATED PATENT APPLICATIONS

This patent application is a national stage of international patent application number PCT/US2016/028980, filed on Apr. 22, 2016, entitled MULTIPLEX METHODS FOR DETECTION AND QUANTIFICATION OF MINOR VARIANTS, naming Anders Olof Herman Nygren as inventor, which claims the benefit of U.S. Provisional Application No. 62/152,698 filed on Apr. 24, 2015, entitled MULTIPLEX METHODS FOR DETECTION AND QUANTIFICATION OF MINOR VARIANTS, naming Anders Nygren as inventor. This patent application is related to U.S. patent application Ser. No. 13/551,486 filed on Jul. 17, 2012, entitled PRODUCTS AND PROCESSES FOR MULTIPLEX NUCLEIC ACID IDENTIFICATION, naming Christiane Honisch, Dirk J. Van Den Boom, Michael Mosko, and Anders Nygren as inventors, which is a continuation application of international patent application no. PCT/US2012/038710 filed on May 18, 2012, entitled PRODUCTS AND PROCESSES FOR MULTIPLEX NUCLEIC ACID IDENTIFICATION, naming Christiane Honisch, Dirk Johannes Van Den Boom, Michael Mosko, and Anders Nygren as inventors. The entire content of the foregoing patent applications hereby is incorporated by reference, including all text, tables and drawings.

FIELD

The technology relates in part to nucleic acid identification procedures in which multiple target nucleic acids can be detected in one procedure. The technology also in part relates to identification of nucleic acid modifications

BACKGROUND

The detection of specific nucleic acids is an important tool for diagnostic medicine and molecular biology research. Nucleic acid assays currently play roles in identifying infectious organisms such as bacteria and viruses, in probing the expression of normal genes and identifying mutant genes such as oncogenes, in typing tissue for compatibility preceding tissue transplantation, in matching tissue or blood samples for forensic medicine, and for exploring homology among genes from different species, for example.

SUMMARY

Provided in certain aspects is a multiplex method for detecting the presence or absence of variants of a plurality of nucleic acid species that include preparing (a) a plurality of amplicons derived from a plurality of target nucleic acid species, or portions thereof, wherein each target nucleic acid species comprises a low-abundance variant and a high-abundance variant. In a single reaction hybridizing the amplicons to a plurality of oligonucleotide species, each oligonucleotide species specifically corresponds to amplicons of a target nucleic acid species, wherein (i) an oligonucleotide species hybridizes to amplicons derived from the low-abundance variant and the high-abundance variant of a target nucleic acid species at a position 5' to a single base position that differs between the low-abundance variant and the high-abundance variant of the target nucleic acid species, (ii) the nucleotide at the single base position is the same or different for each of the high-abundance variants of the plurality of target nucleic acid species, (iii) the nucleotide at the single base position is the same for each of the low-abundance variants of the plurality of target nucleic acid species and (iv) none of the nucleotides at the single base position for the high-abundance variants of the plurality of target nucleic acid species are the same as the nucleotide at the single base position for the low-abundance variants of the plurality of target nucleic acid species; thereby generating hybridized oligonucleotides. Contacting the hybridized oligonucleotides with an extension composition comprising a terminating nucleotide specific for the low-abundance variants and one, two or three terminating nucleotides specific for one or more of the high-abundance variants and under extension conditions; wherein: (i) the terminating nucleotides comprises a capture agent, (ii) the one, two or three terminating nucleotides specific for the high-abundance variants each are at a concentration of from 0.1% to 30% relative to the concentration of the terminating nucleotide specific for the low abundant variants, (iii) the extension conditions comprise multiple thermal cycles, thereby generating extended oligonucleotides comprising a terminating nucleotide specific for the low abundant variants of the plurality of target nucleic acid species and extended oligonucleotides comprising a terminating nucleotide specific for the high-abundance variants of the plurality of target nucleic acid species. Contacting the extended oligonucleotides with a solid phase under conditions in which the capture agent interacts with the solid phase, thereby capturing the extended oligonucleotides onto the solid phase, wherein the solid phase comprises a binding partner of the capture agent and releasing the extended oligonucleotides in by contacting the solid phase at elevated temperature conditions with a competitor, wherein the competitor comprises the free form of the capture agent that interacts with the solid phase. Detecting the extended oligonucleotides released; thereby detecting the presence or absence of the variants of a plurality of nucleic acid species.

Also provided in certain aspects is a method that includes one or more extended oligonucleotides comprising a terminating nucleotide specific for the high-abundance variants as a positive control for a false negative result when an extended oligonucleotide comprising a terminating nucleotide specific for a low-abundance variant is not detected.

Also provided in certain aspects is a method for determining the amount of the low-abundance variant relative to the amount of the high-abundance variant for each target nucleic acid species comprising normalization based on the ratio of the concentration of the terminating nucleotide specific for the low-abundance variant and the concentration of the terminating nucleotide specific for the high-abundance variant.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIG. 1 shows a schematic representation an embodiment of a multiplex method for detecting the presence or absence of variants of a plurality of nucleic acid species. Multiplex PCR is followed by single base extension reactions. The extension reactions consists of a minimum of two chain terminating nucleotides, one targeting the more abundant variant (major variant) and the other targeting less abundant variant (minor variant). In a multiplex reaction in which the major and minor variants for a plurality target nucleic acid species are extended (not shown), up to 4 chain terminating nucleotides targeting every possible base combination can be used (a single terminating nucleotide for the low-abundance variants and either one, two or three distinct terminating nucleotides for the high-abundance variants). The concentration of the chain terminator that targets a major variant is provided at lower concentration (approximately 0.5%-10% of the concentration of the chain terminator for the minor variant) than the concentration of the chain terminator that targets the minor variant. Extension reactions utilize specific chain terminator labeled with a moiety for solid phase capture. After capture and washing, the eluted products are interrogated for mass and the major and minor variants of a target nucleic acid species are identified and characterized using MALDI-TOF mass spectrometry. Quantification is enabled by normalizing the value for the fraction or ratio of minor variant (mutant) signal to major variant (wild type) signal.

DETAILED DESCRIPTION

Methods for determining the presence or absence of a plurality of target nucleic acids described herein find multiple uses by the person of ordinary skill in the art (hereafter referred to herein as the "person of ordinary skill"). Such methods can be utilized, for example, to: (a) rapidly determine whether a particular target sequence (e.g. a target sequence comprising a genetic variation) is present in a sample; (b) perform mixture analysis, e.g., identify a mixture and/or its composition or determine the frequency of a target sequence in a mixture (e.g., mixed communities, quasispecies); (c) detect sequence variations (e.g., mutations, single nucleotide polymorphisms) in a sample; (d) perform haplotyping determinations; (e) perform microorganism (e.g., pathogen) typing; (f) detect the presence or absence of a microorganism target sequence in a sample; (g) identify disease markers; (h) detect microsatellites; (i) identify short tandem repeats; (j) identify an organism or organisms; (k) detect allelic variations; (l) determine allelic frequency; (m) determine methylation patterns; (n) perform epigenetic determinations; (o) re-sequence a region of a biomolecule; (p) perform analyses in human clinical research and medicine (e.g. cancer marker detection, sequence variation detection; detection of sequence signatures favorable or unfavorable for a particular drug administration), (q) perform HLA typing; (r) perform forensics analyses; (s) perform vaccine quality control analyses; (t) monitor treatments; (u) perform vector identity analyses; (v) perform vaccine or production strain quality control and (w) test strain identity (x) plants. Such methods also may be utilized, for example, in a variety of fields, including, without limitation, in commercial, education, medical, agriculture, environmental, disease monitoring, military defense, and forensics fields.

The methods described herein provide a chain terminator specific for the extension of a high-abundance variant (major variant) of a target nucleic acid species at a low concentration along with a chain terminator specific for the extension of a low-abundance variant (minor variant) of a target nucleic acid species at a high concentration. The methods described herein thus provide a positive control for false negative results, allow for the quantification of the low-abundance variant and have a high sensitivity for detecting the presence or absence a low-abundance variant (minor variant). Grouping of a plurality of target nucleic acid species for which the same chain terminator can specifically extend the low-abundance variant (minor variant) of each of the target nucleic acid species allows for multiplexing.

In some embodiments are provided a multiplex method for detecting the presence or absence of variants of a plurality of nucleic acid species, each having a low-abundance variant and a high-abundance variant, that include an amplification reaction, an extension reaction resulting in extended oligonucleotides comprising a terminating nucleotide specific for the low-abundance variants and extended oligonucleotides comprising a terminating nucleotide specific for the high-abundance variants, capture and release of the extended oligonucleotides and detection of the extended oligonucleotides (see FIG. 1). In some embodiments, a positive control for a false negative result is provided. In some embodiments, a method for the quantification of low-abundance variants is provided.

Target Nucleic Acids

As used herein, the term "nucleic acid" refers to an oligonucleotide or polynucleotide, including, without limitation, natural nucleic acids (e.g., deoxyribonucleic acid (DNA), ribonucleic acid (RNA)), synthetic nucleic acids, non-natural nucleic acids (e.g., peptide nucleic acid (PNA)), unmodified nucleic acids, modified nucleic acids (e.g., methylated DNA or RNA, labeled DNA or RNA, DNA or RNA having one or more modified nucleotides). Reference to a nucleic acid as a "polynucleotide" refers to two or more nucleotides or nucleotide analogs linked by a covalent bond. Nucleic acids may be any type of nucleic acid suitable for use with processes described herein. A nucleic acid in certain embodiments can be DNA (e.g., complementary DNA (cDNA), genomic DNA (gDNA), plasmids and vector DNA and the like), RNA (e.g., viral RNA, message RNA (mRNA), short inhibitory RNA (siRNA), ribosomal RNA (rRNA), tRNA and the like), and/or DNA or RNA analogs (e.g., containing base analogs, sugar analogs and/or a non-native backbone and the like). A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, a cell, a cell nucleus or cytoplasm of a cell in certain embodiments. A nucleic acid in some embodiments is from a single chromosome (e.g., a nucleic acid sample may be from one chromosome of a sample obtained from a diploid organism). In the case of fetal nucleic acid, the nucleic acid may be from the paternal allele, the maternal allele or the maternal and paternal allele.

The term "species," as used herein with reference to a target nucleic acid, amplicon, primer, sequence tag, polynucleotide, or oligonucleotide, refers to one nucleic acid having a nucleotide sequence that differs by one or more nucleotides from the nucleotide sequence of another nucleic acid when the nucleotide sequences are aligned. Thus, a first nucleic acid species differs from a second nucleic acid species when the sequences of the two species, when aligned, differ by one or more nucleotides (e.g., about 1, 2, 3, 4, 5, 10, 15, 20, 25, 30, 35, 40, 45, 50, 55, 60, 65, 70, 75, 80, 85, 90, 95, 100 or more than 100 nucleotide differences). In certain embodiments, the number of nucleic acid species, such as target nucleic acid species, amplicon species or extended oligonucleotide species, includes, but is not limited to about 2 to about 10000 nucleic acid species, about 2 to about 1000 nucleic acid species, about 2 to about 500 nucleic acid species, or sometimes about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 600, 700, 800, 900, 1000, 2000, 3000, 4000, 5000, 6000, 7000, 8000, 9000 or 10000 nucleic acid species.

In some embodiments an oligonucleotide species is hybridized to a nucleic acid template (e.g. an amplicon) thereby forming a double stranded nucleic acid and the oligonucleotide species that is hybridized to the template is referred to herein as a hybridized oligonucleotide species. In some embodiments a hybridized oligonucleotide species can comprise one or more nucleotides that are not hybridized to the template. For example, a hybridized oligonucleotide species can comprise one or more mismatched nucleotides (e.g. non-complementary nucleotides) and sometimes a 5' and/or 3' region of nucleotides that do not hybridize. In some embodiments a hybridized oligonucleotide species comprises a tag (e.g. a mass distinguishable tag, a sequence tag, a light emitting tag or a radioactive tag). In some embodiments a hybridized oligonucleotide species comprises a capture agent (e.g. biotin, or any member of binding pair). In some embodiments a hybridized oligonucleotide species comprises a terminating nucleotide.

As used herein, the term "nucleotides" refers to natural and non-natural nucleotides. Nucleotides include, but are not limited to, naturally occurring nucleoside mono-, di-, and triphosphates: deoxyadenosine mono-, di- and triphosphate; deoxyguanosine mono-, di- and triphosphate; deoxythymidine mono-, di- and triphosphate; deoxycytidine mono-, di- and triphosphate; deoxyuridine mono-, di- and triphosphate; and deoxyinosine mono-, di- and triphosphate (referred to herein as dA, dG, dT, dC, dU and dI, or A, G, T, C, U and I respectively). Nucleotides also include, but are not limited to, modified nucleotides and nucleotide analogs. Modified nucleotides and nucleotide analogs include, without limitation, deazapurine nucleotides, e.g., 7-deaza-deoxyguanosine (7-deaza-dG) and 7-deaza-deoxyadenosine (7-deaza-dA) mono-, di- and triphosphates, deutero-deoxythymidine (deutero-dT) mon-, di- and triphosphates, methylated nucleotides e.g., 5-methyldeoxycytidine triphosphate, 13C/15N labeled nucleotides and deoxyinosine mono-, di- and triphosphate. Modified nucleotides, isotopically enriched nucleotides, depleted nucleotides, tagged and labeled nucleotides and nucleotide analogs can be obtained using a variety of combinations of functionality and attachment positions.

The term "composition" as used herein with reference to nucleic acids refers to a tangible item that includes one or more nucleic acids. A composition sometimes is a sample extracted from a source, but also a composition of all samples at the source, and at times is the source of one or more nucleic acids. A composition can comprise nucleic acids. In some embodiments, a composition can comprise genomic DNA. In some embodiments, a composition can comprise maternal DNA, fetal DNA or a mixture of maternal and fetal DNA. In some embodiments, a composition can comprise fragments of genomic DNA. In some embodiments a composition can comprise nucleic acids derived from a virus, bacteria, yeast, fungus, mammal or mixture thereof.

A nucleic acid sample may be derived from one or more sources. A sample may be collected from an organism, mineral or geological site (e.g., soil, rock, mineral deposit, fossil), or forensic site (e.g., crime scene, contraband or suspected contraband), for example. Thus, a source may be environmental, such as geological, agricultural, combat theater or soil sources, for example. A source also may be from any type of organism such as any plant, fungus, protistan, moneran, virus or animal, including but not limited, human, non-human, mammal, reptile, cattle, cat, dog, goat, swine, pig, monkey, ape, gorilla, bull, cow, bear, horse, sheep, poultry, mouse, rat, fish, dolphin, whale, and shark, or any animal or organism that may have a detectable nucleic acids. Sources also can refer to different parts of an organism such as internal parts, external parts, living or non-living cells, tissue, fluid and the like. A sample therefore may be a "biological sample," which refers to any material obtained from a living source or formerly-living source, for example, an animal such as a human or other mammal, a plant, a bacterium, a fungus, a protist or a virus. A source can be in any form, including, without limitation, a solid material such as a tissue, cells, a cell pellet, a cell extract, or a biopsy, or a biological fluid such as urine, blood, saliva, amniotic fluid, exudate from a region of infection or inflammation, or a mouth wash containing buccal cells, hair, cerebral spinal fluid and synovial fluid and organs. A sample also may be isolated at a different time point as compared to another sample, where each of the samples are from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for sequence analysis processes described herein may contain nucleic acid from one sample or from two or more samples (e.g., from 1, 2, 3, 4, 5, 6, 7, 8, 9, 10, 11, 12, 13, 14, 15, 16, 17, 18, 19, 20, 25, 50, 75, 100, 200, 300, 400, 500, 600, 700, 800, 900 or 1000 or more samples).

Nucleic acids may be treated in a variety of manners. For example, a nucleic acid may be reduced in size (e.g., sheared, digested by nuclease or restriction enzyme, de-phosphorylated, de-methylated), increased in size (e.g., phosphorylated, reacted with a methylation-specific reagent, attached to a detectable label), treated with inhibitors of nucleic acid cleavage and the like.

Nucleic acids may be provided for conducting methods described herein without processing, in certain embodiments. In some embodiments, nucleic acid is provided for conducting methods described herein after processing. For example, a nucleic acid may be extracted, isolated, purified or amplified from a sample. The term "isolated" as used herein refers to nucleic acid removed from its original environment (e.g., the natural environment if it is naturally occurring, or a host cell if expressed exogenously), and thus is altered "by the hand of man" from its original environment. An isolated nucleic acid generally is provided with fewer non-nucleic acid components (e.g., protein, lipid) than the amount of components present in a source sample. A composition comprising isolated nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to nucleic acid provided that contains fewer nucleic acid species than in the sample source from which the nucleic acid is derived. A composition comprising nucleic acid may be substantially purified (e.g., about 90%, 91%, 92%, 93%, 94%, 95%, 96%, 97%, 98%, 99% or greater than 99% free of other nucleic acid species).

Nucleic acids may be processed by a method that generates nucleic acid fragments, in certain embodiments, before providing nucleic acid for a process described herein. In some embodiments, nucleic acid subjected to fragmentation or cleavage may have a nominal, average or mean length of about 5 to about 10,000 base pairs, about 100 to about 1,00 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method known in the art, and the average, mean or nominal length of nucleic acid fragments can be controlled by selecting an appropriate fragment-generating procedure. In certain embodiments, nucleic acid of a relatively shorter length can be utilized to analyze sequences that contain little sequence variation and/or contain relatively large amounts of known nucleotide sequence information. In some embodiments, nucleic acid of a relatively longer length can be utilized to analyze sequences that contain greater sequence variation and/or contain relatively small amounts of unknown nucleotide sequence information.

As used herein, the term "target nucleic acid" or "target nucleic acid species" refers to any nucleic acid species of interest in a sample. A target nucleic acid includes, without limitation, (i) a particular allele amongst two or more possible alleles, and (ii) a nucleic acid having, or not having, a particular mutation, nucleotide substitution, sequence variation, repeat sequence, marker or distinguishing sequence. As used herein, the term "different target nucleic acids" refers to nucleic acid species that differ by one or more features. As used herein, the term "genetic variation" refers to nucleic acid species that differ by one or more features. As used herein, the term "variant" refers to nucleic acid species that differ by one or more features. Features include, without limitation, one or more methyl groups or a methylation state, one or more phosphates, one or more acetyl groups, and one or more deletions, additions or substitutions of one or more nucleotides. Examples of one or more deletions, additions or substitutions of one or more nucleotides include, without limitation, the presence or absence of a particular mutation, presence or absence of a nucleotide substitution (e.g., single nucleotide polymorphism (SNP)), presence or absence of a repeat sequence (e.g., di-, tri-, tetra-, penta-nucleotide repeat), presence or absence of a marker (e.g., microsatellite) and presence of absence of a distinguishing sequence (e.g., a sequence that distinguishes one organism from another (e.g., a sequence that distinguishes one viral strain from another viral strain)). Different target nucleic acids may be distinguished by any known method, for example, by mass, binding, distinguishable tags and the like, as described herein.

In some embodiments, one variant can be in greater abundance than other variants. In some embodiments, the variant of greatest abundance is referred to as the wild type variant. In some embodiments a target nucleic acid species comprises a first and second variant where the second variant is represented in greater abundance (more template is present), i.e., a high-abundance variant and a low-abundance variant or major variant and minor variant. A variant that is represented in a greater abundance generally is present at a higher concentration or is represented by a greater number of molecules (e.g. copies) when compared to another variant. A higher concentration can be 2-fold or more. In some embodiments, a higher concentration is 10-fold or more. In some embodiments, a higher concentration is a 100-fold, a 1000-fold or 10000-fold or more. In some embodiments, a second variant represents a wild type sequence and is present at a 100-fold or higher concentration than a first variant. In some embodiments, a first variant (low-abundance variant) is represented at a significantly lower concentration than a second variant (e.g. a wild type, high-abundance variant) where the first variant represents less of the target nucleic acid species. In some embodiments, the methods provided herein can be used to detect the presence or absence of a low-abundance variant that represents less than 30%, 20%, 15%, 10%, 8%, 5%, 4%, 3%, 2%, 1%, 0.8%, 0.75%, 0.5%, 0.1%, 0.05%, 0.01% or less of the target nucleic acid species. In some embodiments, the methods provided herein can be used to detect the presence or absence of a low-abundance variant that represents between about 5% to about 0.75% of the target nucleic acid species. In some embodiments, the methods provided herein can be used to detect the presence or absence of a low-abundance variant that represents less than 30%, 20%, 15%, 10%, 8%, 5%, 4%, 3%, 2%, 1%, 0.8%, 0.75%, 0.5%, 0.1%, 0.05%, 0.01% or less of the total nucleic acid assayed. In some embodiments, the low-abundance variant is present in a copy number of about 1% or about 2% to less than 10% relative to the copy number of the high-abundance variant. In some embodiments, the low-abundance variant is present in a copy number that is 2% or less than the copy number of the high-abundance variant. In some embodiments, for each target nucleic acid species the total copy number of the low-abundance variant and the high-abundance variant is at least about 1000 copies (molecules) and the low-abundance variant represents 0.1% of the total copy number.

As used herein, the term "plurality of target nucleic acids" or "plurality of target nucleic acid species" refers to more than one target nucleic acid species. A plurality of target nucleic acids can be about 2 to about 10000 nucleic acid species, about 2 to about 1000 nucleic acid species, about 2 to about 500 nucleic acid species, or sometimes about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900,1000, 2000, 3000, 4000, 5000, 6000, 7000, 8000, 9000 or 10000 nucleic acid species, in certain embodiments. In certain embodiments, the presence or absence of about 50 or more target nucleic acid species is detected by a method described herein. In some embodiments, about 100 or more, 150 or more, 200 or more, 250 or more, 300 or more, 325 or more, 350 or more, 375 or more, 400, or more, 425 or more, 450 or more, 475 or more or 500 or more target nucleic acids is detected. In some embodiments, the presence, absence or amount of about 2 to 500 target nucleic acid species is detected by a method described herein (e.g., about 5, 10, 25, 50, 75, 100, 150, 200, 250, 300, 350, 400, 450 target nucleic acid species). The target nucleic acids in certain embodiments are genomic DNA (e.g., human, microbial, viral, fungal or plant genomic DNA; any eukaryotic or prokaryotic nucleic acid (RNA and DNA)).

Detection or identification of nucleic acids results in detection of the target and can indicate the presence or absence of a particular mutation, sequence variation (mutation or polymorphism) or genetic variation (e.g. sequence variation, sequence difference or polymorphism). Within the plurality of target nucleic acids, there may be detection of the same or different target nucleic acids. The plurality of target nucleic acids may also be identified quantitatively as well as qualitatively in terms of identification. Also refer to multiplexing below.

Amplification and Extension

A nucleic acid (e.g., a target nucleic acid) can be amplified in certain embodiments. As used herein, the term "amplifying," and grammatical variants thereof, refers to a process of generating copies of a template nucleic acid. For example, nucleic acid template may be subjected to a process that linearly or exponentially generates two or more nucleic acid amplicons (copies) having the same or substantially the same nucleotide sequence as the nucleotide sequence of the template, or a portion of the template. Nucleic acid amplification often is specific (e.g., amplicons have the same or substantially the same sequence), and can be non-specific (e.g., amplicons have different sequences) in certain embodiments. Nucleic acid amplification sometimes is beneficial when the amount of target sequence present in a sample is low. By amplifying the target sequences and detecting the amplicon synthesized, sensitivity of an assay can be improved, since fewer target sequences are needed at the beginning of the assay for detection of a target nucleic acid. A target nucleic acid sometimes is not amplified prior to hybridizing an extension oligonucleotide, in certain embodiments.

Amplification conditions are known and can be selected for a particular nucleic acid that will be amplified. Amplification conditions include certain reagents some of which can include, without limitation, nucleotides (e.g., nucleotide triphosphates), modified nucleotides, oligonucleotides (e.g., primer oligonucleotides for polymerase-based amplification and oligonucleotide building blocks for ligase-based amplification), one or more salts (e.g., magnesium-containing salt), one or more buffers, one or more polymerizing agents (e.g., ligase enzyme, polymerase enzyme), one or more nicking enzymes (e.g., an enzyme that cleaves one strand of a double-stranded nucleic acid) and one or more nucleases (e.g., exonuclease, endonuclease, RNase). Any polymerase suitable for amplification may be utilized, such as a polymerase with or without exonuclease activity, DNA polymerase and RNA polymerase, mutant forms of these enzymes, for example. Any ligase suitable for joining the 5' of one oligonucleotide to the 3' end of another oligonucleotide can be utilized. Amplification conditions also can include certain reaction conditions, such as isothermal or temperature cycle conditions. Methods for cycling temperature in an amplification process are known, such as by using a thermocycle device. The term "cycling" refers to amplification (e.g. an amplification reaction or extension reaction) utilizing a single primer or multiple primers where temperature cycling is used. Amplification conditions also can, in some embodiments, include an emulsion agent (e.g., oil) that can be utilized to form multiple reaction compartments within which single nucleic acid molecule species can be amplified. Amplification is sometimes an exponential product generating process and sometimes is a linear product generating process.

In some embodiments an amplification reaction includes multiple temperature cycles repeated to amplify the amount of target nucleic acid species. In some embodiments the amplification reaction is cycled 2 or more times. In some embodiments the amplification reaction is cycled 10 or more times. In some embodiments the amplification reaction is cycled about 10, 15, 20, 50, 100, 200, 300 or more times. In some embodiments the amplification reaction is cycled 20 to 50 times. In some embodiments the amplification reaction is cycled 30 to 45 times.

A strand of a single-stranded nucleic acid target can be amplified and one or two strands of a double-stranded nucleic acid target can be amplified. An amplification product (amplicon), in some embodiments, is about 10 nucleotides to about 10,000 nucleotides in length, about 10 to about 1000 nucleotides in length, about 10 to about 500 nucleotides in length, 10 to about 100 nucleotides in length, and sometimes about 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 nucleotides in length.

Any suitable amplification technique and amplification conditions can be selected for a particular nucleic acid for amplification. Known amplification processes include, without limitation, polymerase chain reaction (PCR), extension and ligation, ligation amplification (or ligase chain reaction (LCR)) and amplification methods based on the use of Q-beta replicase or template-dependent polymerase (see US Patent Publication Number US20050287592). Also useful are strand displacement amplification (SDA), thermophilic SDA, nucleic acid sequence based amplification (3SR or NASBA) and transcription-associated amplification (TAA). Reagents, apparatus and hardware for conducting amplification processes are commercially available, and amplification conditions are known and can be selected for the target nucleic acid at hand.

Polymerase-based amplification can be effected, in certain embodiments, by employing universal primers. In such processes, hybridization regions that hybridize to one or more universal primers are incorporated into a template nucleic acid. Such hybridization regions can be incorporated into (i) a primer that hybridizes to a target nucleic acid and is extended, and/or (ii) an oligonucleotide that is joined (e.g., ligated using a ligase enzyme) to a target nucleic acid or a product of (i), for example. Amplification processes that involve universal primers can provide an advantage of amplifying a plurality of target nucleic acids using only one or two amplification primers, for example.

Certain nucleic acids can be extended in certain embodiments. The term "extension," and grammatical variants thereof, as used herein refers to elongating one strand of a nucleic acid. For example, an oligonucleotide that hybridizes to a target nucleic acid or an amplicon generated from a target nucleic acid can be extended in certain embodiments. An extension reaction is conducted under extension conditions, and a variety of such conditions are known and selected for a particular application. Extension conditions include certain reagents, including without limitation, one or more oligonucleotides, extension nucleotides (e.g., nucleotide triphosphates (dNTPs)), terminating nucleotides (e.g., one or more dideoxynucleotide triphosphates (ddNTPs)), one or more salts (e.g., magnesium-containing salt), one or more buffers (e.g., with beta-NAD, Triton X-100), and one or more polymerizing agents (e.g., DNA polymerase, RNA polymerase). Extension can be conducted under isothermal conditions or under non-isothermal conditions (e.g., thermocycled conditions), in certain embodiments. One or more nucleic acid species can be extended in an extension reaction, and one or more molecules of each nucleic acid species can be extended. A nucleic acid can be extended by one or more nucleotides, and in some embodiments, the extension product is about 10 nucleotides to about 10,000 nucleotides in length, about 10 to about 1000 nucleotides in length, about 10 to about 500 nucleotides in length, 10 to about 100 nucleotides in length, and sometimes about 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 nucleotides in length. Incorporation of a terminating nucleotide (e.g., ddNTP), the hybridization location, or other factors, can determine the length to which the oligonucleotide is extended. In certain embodiments, amplification and extension processes are carried out in the same detection procedure.

In some embodiments an extension reaction includes multiple temperature cycles repeated to amplify the amount of extension product in the reaction. In some embodiments the extension reaction is cycled 2 or more times. In some embodiments the extension reaction is cycled 10 or more times. In some embodiments the extension reaction is cycled about 10, 15, 20, 50, 100, 200, 300, 400, 500 or 600 or more times. In some embodiments the extension reaction is cycled 20 to 50 times. In some embodiments the extension reaction is cycled 20 to 100 times. In some embodiments the extension reaction is cycled 20 to 300 times. In some embodiments the extension reaction is cycled at least 50 times.

In some embodiments a target nucleic acid (e.g. target nucleic acid species, oligonucleotide species, hybridized oligonucleotide species or amplicon) is extended in the presence of an extension composition where the target nucleic acid is extended by one nucleotide. An extension composition can comprise one or more buffers, salts, enzymes (e.g. polymerases, Klenow, etc.), water, templates (e.g. DNA, RNA, amplicons, etc.), primers (e.g. oligonucleotides), nucleotide triphosphates, glycerol, macromolecular exclusion molecules and any other additives used in the art. An extension composition can comprise terminating nucleotides (e.g. dideoxynucleotides (e.g. ddNTPs)), non-terminating or extension nucleotides (e.g. dNTPs) or a mixture of terminating nucleotides and non-terminating nucleotides. An extension composition consisting essentially of a particular terminating nucleotide or terminating nucleotides, can contain any other component of an extension composition (e.g. buffers, salts, templates, primers, etc.), but does not contain any other terminating nucleotide or nucleotide triphosphate (e.g. dNTP) except those specified. For example an extension composition consisting essentially of ddTTP and ddCTP does not contain ddATP, ddGTP or any other dNTP. In some embodiments the nucleotides in an extension composition are only terminating nucleotides and the target nucleic acid is extended by one nucleotide (i.e. sometimes there are no extension nucleotides in the extension composition). In some embodiments an extension composition consists essentially of terminating nucleotides (e.g. ddNTPs). In some embodiments, a terminating nucleotide comprises one or more (e.g. 1, 2, 3, 4, 5, 6, 7, 8, 9, 10, 11, 12, 13, 14, 15, 20, or more) capture agents. In some embodiments, a terminating nucleotide comprises one or more (e.g. 1, 2, 3, 4, 5, 6, 7, 8, 9, 10, 11, 12, 13, 14, 15, 20, or more) different capture agents. In some embodiments, a terminating nucleotide comprises (e.g. is covalently bound to) one or more (e.g. 1, 2, 3, 4, 5, 6, 7, 8, 9, 10, 11, 12, 13, 14, 15, 20, or more) capture agent molecules. In some embodiments, a terminating nucleotide comprises one capture agent molecule. In some embodiments, a first terminating nucleotide comprises a capture agent and a second terminating nucleotide comprises a different capture agent. In some embodiments, an extension composition comprises one or more terminating nucleotides where each terminating nucleotide comprises a different capture agent. In some embodiments, an extension composition comprises one or more terminating nucleotides where each terminating nucleotide comprises a capture agent and the capture agent is the same. In some embodiments, an extension composition comprises a terminating nucleotide and an extension nucleotide and one or more of the nucleotides (e.g. terminating nucleotides and/or extension nucleotides) include a capture agent. In some embodiments a terminating nucleotide comprises a capture agent and the capture agent is biotin or a biotin analogue. In some embodiments, the extension composition consists essentially of terminating nucleotides that are bound to one or more capture agents. In some embodiments the capture agent is biotin or a biotin analogue.

Any suitable extension reaction can be selected and utilized. An extension reaction can be utilized, for example, to discriminate SNP alleles by the incorporation of deoxynucleotides and/or dideoxynucleotides to an extension oligonucleotide that hybridizes to a region adjacent to the SNP site in a target nucleic acid. The primer often is extended with a polymerase. In some embodiments, the oligonucleotide is extended by only one deoxynucleotide or dideoxynucleotide complementary to the SNP site. In some embodiments, an oligonucleotide may be extended by dNTP incorporation and terminated by a ddNTP, or terminated by ddNTP incorporation without dNTP extension in certain embodiments. One or more dNTP and/or ddNTP used during the extension reaction are labeled with a moiety allowing immobilization to a solid support, such as biotin, in some embodiments. Extension may be carried out using unmodified extension oligonucleotides and unmodified dideoxynucleotides, unmodified extension oligonucleotides and biotinylated dideoxynucleotides, extension oligonucleotides containing a deoxyinosine and unmodified dideoxynucleotides, extension oligonucleotides containing a deoxyinosine and biotinylated dideoxynucleotides, extension by biotinylated dideoxynucleotides, or extension by biotinylated deoxynucleotide and/or unmodified dideoxynucleotides, in some embodiments.

In some embodiments an oligonucleotide species can hybridize, under hybridization conditions, to a template (e.g. a target nucleic acid species) adjacent to a genetic variation or variant (e.g. the 3' end of the oligonucleotide species may be located 5' of the genetic variation site and may be 0 to 10 nucleotides away from the 5' end of the genetic variation site). Several variant may exist at a site of genetic variation in a target nucleic acid. A genetic variant sometimes is a single nucleotide polymorphism (SNP) or single nucleotide variant. Several single nucleotide variants may exist at a single base position on a template target located 3' of a hybridized oligonucleotide. Several single nucleotide variants may differ by a single base located at a position on a template target that is 3' of a hybridized oligonucleotide species. In some embodiments an oligonucleotide species is extended by one nucleotide at the variant position. The oligonucleotide can be extended by any one of five terminating nucleotides (e.g. ddATP, ddUTP, ddTTP, ddGTP, ddCTP), depending on the number of variants present, in some embodiments. A target nucleic acid species and its variants, or a corresponding amplicon, can act as the template and can, in part, determine which terminating nucleotide is added to the oligonucleotide in the extension reaction.

In some embodiments the amount of a target species low-abundance variant relative to the amount of a target species high-abundance variant (e.g., wild type) present in an assay is determined based on detection of the extended oligonucleotides representing the low-abundance variant and the high-abundance variant. Because the incorporation of the high-abundance terminating nucleotide is suppressed, but still linear, a normalization coefficient is necessary for quantifying the true ratio between the high and low-abundance variants. In some embodiments the amount (e.g. copy number, concentration, percentage) of low-abundance variant of a target nucleic acid species is quantified by normalizing the ratio of the signal for the low-abundance variant to the signal for the high-abundance variant using a coefficient. The coefficient is inversely proportional to the fractional value of the concentration of the terminating nucleotide specific for the high-abundance variant compared to the concentration of the terminating nucleotide specific for the low-abundance variant, i.e., the lower the fractional value for the high-abundance variant specific terminating nucleotide the higher the coefficient.

In some embodiments, a terminating nucleotide that is present (or, in some embodiments absent) in an extension composition determines which terminating nucleotide is added to an oligonucleotide. In some embodiments, an extension composition comprises one or more terminating nucleotides (e.g. ddNTPs). In some embodiments, an extension composition comprises one or more terminating nucleotides and one or more non-terminating nucleotides (e.g. dNTPs). In some embodiments, an extension composition comprises terminating nucleotides that correspond to a specific variant (e.g. a first variant, minor variant or low-abundance variant) and therefore only allow extension of that specific variant. In some embodiments, a terminating nucleotide that would allow extension of a second variant (e.g. a wild type, major variant or high-abundance variant) is included in an extension composition thereby allowing for the extension of the second variant. In some embodiments, a method comprises contacting hybridized oligonucleotide species with an extension composition comprising one or more terminating nucleotides under extension conditions where (i) at least one of the one or more terminating nucleotides comprises a capture agent, and (ii) the hybridized oligonucleotide species that hybridize to the first variant (e.g. a low-abundance variant, less abundant SNP variant, minor variant) are extended by a terminating nucleotide and the hybridized oligonucleotide species that hybridize to the second variant (e.g. wild type, high-abundance variant, major variant) are extended by a terminating nucleotide, thereby generating extended oligonucleotide species.

The term "signal to noise ratio" as used herein refers to the quantitative measurement of the quality of a signal by quantifying the ratio of intensity of a signal relative to noise when using a detection process (e.g. mass spectrometry). In some embodiments, an intensive peak on one spectrum has a greater signal to noise ratio than a low intensity peak generated by the same analyte (e.g. an extended oligonucleotide species) on another spectrum. In some embodiments, noise is generated by extended oligonucleotide species derived from the high-abundance variants (e.g. wild type alleles, second variants, wild type variants). In some embodiments, the signal generated from an extended oligonucleotide species derived from a low-abundance variant (e.g. a first variant, minor variant, mutant variant, mutant allele, SNP) is obscured by the noise generated by a more abundant extended oligonucleotide species (e.g. a second variant, high-abundance variant, major variant, wild type variant, wild type allele), for example when using mass spectrometry. The term "signal" as used in the phrase "signal to noise ratio" herein refers to the intensity of a signal peak of an extended oligonucleotide species. In some embodiments, the term "signal" as used in the phrase "signal to noise ratio" herein generally refers to the intensity of a signal peak of an extended oligonucleotide species derived from a less abundant variant (e.g. a first variant, low-abundance variant, mutant variant, mutant allele, SNP). In some embodiments, a terminating nucleotide that would allow extension of a high-abundance variant (e.g., a second variant, a wild type or more abundant variant) is included in an extension composition at a much lower concentration than the terminating nucleotide that allows extension for the low-abundance variant (i.e., an adjusted or skewed concentration) thereby not reducing the signal to noise ratio for a low-abundance variant (e.g. a first variant, mutant variant, mutant allele, SNP). In some embodiments, a method comprises contacting hybridized oligonucleotide species with an extension composition comprising one or more terminating nucleotides under extension conditions where (i) at least one of the one or more terminating nucleotides comprises a capture agent, and (ii) the hybridized oligonucleotide species that hybridize to the low-abundance variant (e.g., minor variant, less abundant SNP variant) are extended by a terminating nucleotide and the hybridized oligonucleotide species that hybridize to the high-abundance variant (e.g. wild type or major variant) are extended by a terminating nucleotide that is provided at a lower concentration than the concentration of the terminating nucleotide for the low-abundance variant, thereby not diminishing the signal to noise ratio compared to a condition where only the low-abundance variant in the absence of extending is the high abundance variant.

In some embodiments the detecting in (f) is with a signal to noise ratio greater than a signal to noise ratio for detecting after releasing without competition with a competitor. In some embodiments the detecting in (f) comprises an increase in a signal to noise ratio when the releasing step (e) comprises competition with a competitor as compared to a releasing step that does not comprise competition with a competitor.

In some embodiments, utilizing a skewed or adjusted terminating concentration and a competitor enables enhanced detection of a low-abundance or minor variant. In some embodiments, a low-abundance or minor variant can be detected at a copy number that is 2% or less than the copy number the high-abundance variant. The limit of detection of a low-abundance variant is about 0.1% abundance. A low-abundance variant below 3% abundance can be quantified. Quantification of a low-abundance variant with an abundance above 5% is hindered as the high signal obtained from the low-abundance variant diminishes the signal from the high-abundance variant.

The term "sensitivity" as used herein refers to an amount of analyte that can be detected at a given signal-to-noise ratio when using a detection process (e.g. mass spectrometry). In some embodiments, sensitivity can be improved by decreasing the background or noise level. In some embodiments, noise is generated by extended oligonucleotide species derived from more abundant variants (e.g. wild type alleles, second variants, wild type variants). In some embodiments, sensitivity is increased when the signal generated from an extended oligonucleotide species derived from a more abundant extended oligonucleotide species (e.g. a second variant, wild type variant, wild type allele) is detected but reduced in intensity. In some embodiments, a terminating nucleotide that would allow extension of a more abundant variant (e.g. a wild type, high-abundance variant, major variant) is included in an extension composition at a reduced concentration that does not decrease the sensitivity for detection of a low-abundance variant (e.g. a minor variant, mutant variant, mutant allele, SNP). In certain embodiments, the terminating nucleotide specific for the high-abundance variants is at a concentration of 10% or less relative to the concentration of the terminating nucleotide specific for the low-abundance variants. In certain embodiments, the terminating nucleotide specific for the high-abundance variants is between about 0.5% to less than about 20%, about 0.5% to less than about 15%, about 1% to about 15%, about 1% to about 10% or about 2% to about 10% of the concentration of the terminating nucleotide specific for the low-abundance variants. In certain embodiments, the terminating nucleotide specific for the high-abundance variants is at a concentration of from 0.1% to 30% relative to the concentration of the terminating nucleotide specific for the low-abundance variants. In certain embodiments, the terminating nucleotide specific for the high-abundance variants is at a concentration of from 0.5% to 10% relative to the concentration of the terminating nucleotide specific for the low-abundance variants. In certain embodiments, the terminating nucleotide specific for the high-abundance variants is at a concentration of from 1% to 2% relative to the concentration of the terminating nucleotide specific for the low-abundance variants.

Any suitable type of nucleotides can be incorporated into an amplification product or an extension product. Nucleotides may be naturally occurring nucleotides, terminating nucleotides, or non-naturally occurring nucleotides (e.g., nucleotide analog or derivative), in some embodiments. Certain nucleotides can comprise a detectable label and/or a member of a binding pair (e.g., the other member of the binding pair may be linked to a solid phase), in some embodiments.

A solution containing amplicons produced by an amplification process, or a solution containing extension products produced by an extension process, can be subjected to further processing. For example, a solution can be contacted with an agent that removes phosphate moieties from free nucleotides that have not been incorporated into an amplicon or extension product. An example of such an agent is a phosphatase (e.g., alkaline phosphatase). In some embodiments, alkaline phosphatase is shrimp alkaline phosphatase. Amplicons and extension products also may be associated with a solid phase, may be washed, may be contacted with an agent that removes a terminal phosphate (e.g., exposure to a phosphatase), may be contacted with an agent that removes a terminal nucleotide (e.g., exonuclease), may be contacted with an agent that cleaves (e.g., endonuclease, ribonuclease), and the like.

The term "oligonucleotide" as used herein refers to two or more nucleotides or nucleotide analogs linked by a covalent bond. An oligonucleotide is of any convenient length, and in some embodiments is about 5 to about 200 nucleotides in length, about 5 to about 150 nucleotides in length, about 5 to about 100 nucleotides in length, about 5 to about 75 nucleotides in length or about 5 to about 50 nucleotides in length, and sometimes is about 5, 6, 7, 8, 9, 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, or 200 nucleotides in length. Oligonucleotides may include deoxyribonucleic acid (DNA), ribonucleic acid (RNA), naturally occurring and/or non-naturally occurring nucleotides or combinations thereof and any chemical or enzymatic modification thereof (e.g. methylated DNA, DNA of modified nucleotides). The length of an oligonucleotide sometimes is shorter than the length of an amplicon or target nucleic acid, but not necessarily shorter than a primer or polynucleotide used for amplification. An oligonucleotide often comprises a nucleotide subsequence or a hybridization sequence that is complementary, or substantially complementary, to an amplicon, target nucleic acid or complement thereof (e.g., about 95%, 96%, 97%, 98%, 99% or greater than 99% identical to the amplicon or target nucleic acid complement when aligned). An oligonucleotide may contain a nucleotide subsequence not complementary to, or not substantially complementary to, an amplicon, target nucleic acid or complement thereof (e.g., at the 3' or 5' end of the nucleotide subsequence in the primer complementary to or substantially complementary to the amplicon). An oligonucleotide in certain embodiments, may contain a detectable molecule (e.g., a tag, fluorophore, radioisotope, colormetric agent, particle, enzyme and the like) and/or a member of a binding pair, in certain embodiments (e.g., biotin/avidin, biotin/streptavidin).

The term "in solution" as used herein refers to a liquid, such as a liquid containing one or more nucleic acids, for example. Nucleic acids and other components in solution may be dispersed throughout, and a solution often comprises water (e.g., aqueous solution). A solution may contain any convenient number of oligonucleotide species, and there often are at least the same number of oligonucleotide species as there are amplicon species or target nucleic acid species to be detected.

The term "hybridization sequence" as used herein refers to a nucleotide sequence in an oligonucleotide capable of specifically hybridizing to an amplicon, target nucleic acid or complement thereof. The hybridization sequence is readily designed and selected and can be of a length suitable for hybridizing to an amplicon, target sequence or complement thereof in solution as described herein. In some embodiments, the hybridization sequence in each oligonucleotide is about 5 to about 200 nucleotides in length (e.g., about 5 to 10, about 10 to 15, about 15 to 20, about 20 to 25, about 25 to 30, about 30 to 35, about 35 to 40, about 40 to 45, or about 45 to 50, about 50 to 70, about 80 to 90, about 90 to 110, about 100 to 120, about 110 to 130, about 120 to 140, about 130 to 150, about 140 to 160, about 150 to 170, about 160 to 180, about 170 to 190, about 180 to 200 nucleotides in length).

The term "hybridization conditions" as used herein refers to conditions under which two nucleic acids having complementary nucleotide sequences can interact with one another. Hybridization conditions can be high stringency, medium stringency or low stringency, and conditions for these varying degrees of stringency are known. Hybridization conditions often are selected that allow for amplification and/or extension depending on the application of interest.

The term "specifically hybridizing to one amplicon or target nucleic acid" as used herein refers to hybridizing substantially to one amplicon species or target nucleic acid species and not substantially hybridizing to other amplicon species or target nucleic acid species in the solution. Specific hybridization rules out mismatches so that, for example, an oligonucleotide may be designed to hybridize specifically to a certain allele and only to that allele. An oligonucleotide that is homogenously matched or complementary to an allele will specifically hybridize to that allele, whereas if there is one or more base mismatches then no hybridization may occur.

The term "hybridization location" as used herein refers to a specific location on an amplicon or target nucleic acid to which another nucleic acid hybridizes. In certain embodiments, the terminus of an oligonucleotide is adjacent to or substantially adjacent to a site on an amplicon species or target nucleic acid species that has a different sequence than another amplicon species or target nucleic acid species. The terminus of an oligonucleotide is "adjacent" to a site when there are no nucleotides between the site and the oligonucleotide terminus. The terminus of an oligonucleotide is "substantially adjacent" to a site when there are 1, 2, 3, 4, 5, 6, 7, 8, 9 or 10 nucleotides between the site and the oligonucleotide terminus, in certain embodiments.

Capture Agents and Solid Phases

One or more capture agents may be utilized for the methods described herein. There are several different types of capture agents available for processes described herein, including, without limitation, members of a binding pair, for example. Examples of binding pairs, include, without limitation, (a) non-covalent binding pairs (e.g., antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, receptor/ligand or binding portion thereof, and vitamin B12/intrinsic factor); and (b) covalent attachment pairs (e.g., sulfhydryl/maleimide, sulfhydryl/haloacetyl derivative, amine/isotriocyanate, amine/succinimidyl ester, and amine/sulfonyl halides), and the like. In some embodiments, one member of a binding pair is in association with an extended oligonucleotide or amplification product and another member in association with a solid phase. The term "in association with" as used herein refers to an interaction between at least two units, where the two units are bound or linked to one another, for example.

In certain embodiments, the capture agent includes a member of a binding pair. In some embodiments, the capture agent includes biotin or a biotin analogue, and on certain embodiments, the solid phase includes avidin or streptavidin. In some embodiments, the capture agent includes avidin or streptavidin, and in certain embodiments, the solid phase includes biotin. In certain embodiments, (c) (e.g., generating extended oligonucleotides that include a capture agent by extending oligonucleotides hybridized to the amplicons by one or more nucleotides, wherein one of the one of more nucleotides is a terminating nucleotide and one or more of the nucleotides added to the oligonucleotides includes the capture agent.

In some embodiments, the terminal nucleotides in the extended oligonucleotides comprise the capture agent. In certain embodiments, one or more non-terminal nucleotides in the extended oligonucleotides comprise the capture agent. In some embodiments, the hybridization sequence is about 5 to about 200 nucleotides in length. In some embodiments, the hybridization sequence in each oligonucleotide is about 5 to about 50 nucleotides in length. In certain embodiments, terminal nucleotides in the extended oligonucleotides comprise the capture agent, and sometimes one or more non-terminal nucleotides in the extended oligonucleotides comprise the capture agent. In some embodiments, the capture agent comprises biotin, or alternatively avidin or streptavidin, in which case the solid phase comprises avidin or streptavidin, or biotin, respectively.

A biotin analogue can be any modified biotin that effects the binding properties of biotin to avidin or streptavidin (e.g. 9-methylbiotin, biotin methyl ester (MEBio), desthiobiotin (DEBio), 2'-iminobiotin (IMBio), e-N-Biotinyl-L-lysine, diaminobiotin (DABio), including all biotin analogues disclosed in Lai-Qiang et. al. (Lai-Qiang Ying and Bruce P. Branchaud, Chemical Communications, 2011, 47, 8593-8595)). In some embodiments the capture agent is avidin, streptavidin or a modified form of avidin or streptavidin (e.g. nitroavidin, nitrostreptavidin, NeutrAvidin, CaptAvidin and derivatives thereof).

The term "competitor" as used herein refers to any molecule that competes with the capture agent for interaction with (e.g., binding to) the solid phase. Non-limiting examples of competitors include free capture agent (e.g., one or the other member of a binding pair, free biotin, free avidin/streptavidin), a competing fragment of a capture agent (e.g., a competing fragment of biotin or avidin/streptavidin), a competing multimer of the capture agent (e.g., a biotin multimer), another competing molecule or fragment or multimer thereof, a molecule that competes specifically for binding to the solid phase, elevated salt conditions, elevated temperature conditions, or combinations thereof. In some embodiments, a multimer of a capture agent comprises between about 2 and about 50 monomers. In some embodiments, a multimer of a capture agent comprises between about 2 and about 10 monomers. In some embodiments, a multimer of a capture agent comprises about 2, 3, 4, 5, 6, 7, 8, 9, 10, 11, 12, 13, 14, 15, 16, 17, 18, 19, or 20 monomers. In some embodiments, a capture agent comprising a multimer of capture agents comprises monomers that are covalently bound to each other. In some embodiments, a capture agent comprising a multimer of capture agents comprises monomers that are not covalently bound to each other. The term "free capture agent" as used herein refers to a capture agent that is not in association with a solid phase or extended oligonucleotide. In some embodiments, a free capture agent can be biotin or a competing portion or fragment thereof. In certain embodiments, a free capture agent can be avidin, streptavidin, or a competing portion or fragment thereof. The term "competing portion or fragment" refers to capture agent that is less than full size, yet still retains the functionality of the intact capture agent (e.g., the same, less or more of the capture agent interaction activity with the solid support) with respect to interaction with the other member of a binding pair (e.g., a fragment or portion of biotin that still can bind to avidin or streptavidin, a fragment or portion of avidin or streptavidin that still can bind to biotin). In some embodiments, a fragment of a free capture agent (e.g. a fragment of biotin), is any size that still retains the functionality of the intact capture agent. In some embodiments, a free capture agent (e.g. a fragment of biotin), is any size that still retains some of the functionality of the intact capture agent. In some embodiments, a free capture agent (e.g. a fragment of biotin), is a size that retains between about 30% and about 100% of the functionality of the intact capture agent. In some embodiments, a free capture agent (e.g. a fragment of biotin), is a size that retains about 30%, 40%, 50%, 60%, 70%, 80%, 90% or 100% of the functionality of the intact capture agent.

In some embodiments, free capture agent (e.g. free biotin) is added at a concentration from about 0.1 to about 5000 ug/ml. In some embodiments, free capture agent (e.g. free biotin) is added at a concentration of about 0.1, 0.25, 0.5, 1, 2.5, 5, 10, 20, 25, 30, 40, 50, 60, 70, 80, 90, 100, 200, 400, 800, 1000, 2000, 4000, 5000 ug/ml or higher. In some embodiments, free capture agent (e.g. free biotin) is added at a concentration from about 10 to about 100 ug/ml. In some embodiments, free capture agent (e.g. free biotin) is added at a concentration of about 10, 20, 21, 22, 23, 24, 25, 26, 27, 28, 29, or 30 ug/ml. In some embodiments, free capture agent (e.g. free biotin) is added to a composition comprising an extended oligonucleotides species at a concentration of about 25 ug/ml.

In some embodiments, releasing the extended oligonucleotides is by competition with a competitor is carried out under elevated temperature conditions. In certain embodiments, the elevated temperature conditions include treatment for between about 1 minute to about 10 minutes (e.g., about 1 minute, about 2 minutes about 3 minutes, about 4 minutes, about 5 minutes, about 6 minutes, about 7 minutes, about 8 minutes, about 9 minutes or about 10 minutes) at a temperature of between about 80 degrees Celsius to about 100 degrees Celsius (e.g., about 80 degrees Celsius (° C.), about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., or 100° C.). In some embodiments, the elevated temperature conditions comprise treatment for about 5 minutes at about 90 degrees Celsius.

The term "solid support" or "solid phase" as used herein refers to an insoluble material with which nucleic acid can be associated. Examples of solid supports for use with processes described herein include, without limitation, arrays, beads (e.g., paramagnetic beads, magnetic beads, microbeads, nanobeads) and particles (e.g., microparticles, nanoparticles). Particles or beads having a nominal, average or mean diameter of about 1 nanometer to about 500 micrometers can be utilized, such as those having a nominal, mean or average diameter, for example, of about 10 nanometers to about 100 micrometers; about 100 nanometers to about 100 micrometers; about 1 micrometer to about 100 micrometers; about 10 micrometers to about 50 micrometers; about 1, 5, 10, 15, 20, 25, 30, 35, 40, 45, 50, 55, 60, 65, 70, 75, 80, 85, 90, 95, 100, 200, 300, 400, 500, 600, 700, 800 or 900 nanometers; or about 1, 5, 10, 15, 20, 25, 30, 35, 40, 45, 50, 55, 60, 65, 70, 75, 80, 85, 90, 95, 100, 200, 300, 400, 500 micrometers. The term "paramagnetic" as used herein refers to magnetism that generally occurs only in the presence of an externally applied magnetic field. Thus, a paramagnetic bead can be attracted to an externally applied magnetic source, but typically does not exert its own magnetic field in the absence of an externally applied magnetic field. Magnetic beads comprising a ferrous core, generally exert their own magnetic field.

In certain embodiments, the solid phase is selected from a flat surface, a silicon chip, a bead, sphere or combination of the foregoing. A solid phase sometimes is paramagnetic. In some embodiments, the solid phase is a paramagnetic bead, and in certain embodiments, the solid phase includes a capture agent.

A solid support can comprise virtually any insoluble or solid material, and often a solid support composition is selected that is insoluble in water. For example, a solid support can comprise or consist essentially of silica gel, glass (e.g. controlled-pore glass (CPG)), nylon, Sephadex®, Sepharose®, cellulose, a metal surface (e.g. steel, gold, silver, aluminum, silicon and copper), a magnetic material, a plastic material (e.g., polyethylene, polypropylene, polyamide, polyester, polyvinylidenedifluoride (PVDF)) and the like. Beads or particles may be swellable (e.g., polymeric beads such as Wang resin) or non-swellable (e.g., CPG). Commercially available examples of beads include without limitation Wang resin, Merrifield resin and Dynabeads® and SoluLink. A solid phase (e.g. a bead) can comprise a member of a binding pair (e.g. avidin, streptavidin or derivative thereof). In some embodiments a solid phase is substantially hydrophilic. In some embodiments a solid phase (e.g. a bead) is substantially hydrophobic. In some embodiments a solid phase comprises a member of a binding pair (e.g. avidin, streptavidin or derivative thereof) and is substantially hydrophobic or substantially hydrophilic. In some embodiments, a solid phase comprises a member of a binding pair (e.g. avidin, streptavidin or derivative thereof) and has a binding capacity greater than about 1350 pmoles of free capture agent (e.g. free biotin) per mg solid support. In some embodiments the binding capacity of solid phase comprising a member of a binding pair is greater than 800, 900, 1000, 1100, 1200, 1250, 1300, 1350, 1400, 1450, 1500, 1600, 1800, 2000 pmoles of free capture agent per mg solid support.

A solid support may be provided in a collection of solid supports. A solid support collection comprises two or more different solid support species. The term "solid support species" as used herein refers to a solid support in association with one particular solid phase nucleic acid species or a particular combination of different solid phase nucleic acid species. In certain embodiments, a solid support collection comprises 2 to 10,000 solid support species, 10 to 1,000 solid support species or about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 unique solid support species. The solid supports (e.g., beads) in the collection of solid supports may be homogeneous (e.g., all are Wang resin beads) or heterogeneous (e.g., some are Wang resin beads and some are magnetic beads). Each solid support species in a collection of solid supports sometimes is labeled with a specific identification tag. An identification tag for a particular solid support species sometimes is a nucleic acid (e.g., "solid phase nucleic acid") having a unique sequence in certain embodiments. An identification tag can be any molecule that is detectable and distinguishable from identification tags on other solid support species.

After extended oligonucleotides are associated with a solid phase (i.e. post capture), unextended oligonucleotides and/or unwanted reaction components that do not bind often are washed away or degraded. In some embodiments, a solid phase is washed after extended oligonucleotide species are captured. In some embodiments, a solid phase is washed after extended oligonucleotide species are captured and prior to releasing the extended oligonucleotide species. In some embodiments, washing a solid phase removes salts. In some embodiments, washing a solid phase removes salts that produce interfering adducts in mass spectrometry. In some embodiments, washing a solid phase removes salts that interfere with mass spectrometry. In some embodiments, extended oligonucleotide species are contacted with an anion exchange resin after washing the solid phase. In some embodiments, extended oligonucleotide species are not contacted with an anion exchange resin after washing the solid phase. In some embodiments, extended oligonucleotide species are captured on a solid phase, washed one or more times, released from the solid phase and are not contacted with an anion exchange resin. Extended oligonucleotides may be treated by one or more procedures prior to detection. For example, extended oligonucleotides may be conditioned prior to detection (e.g., homogenizing the type of cation and/or anion associated with captured nucleic acid by ion exchange). Extended oligonucleotides may be released from a solid phase prior to detection in certain embodiments.

In some embodiments, an extended oligonucleotide (e.g. an extended oligonucleotide species) is in association with a capture agent comprising one member of a binding pair (e.g., biotin or avidin/streptavidin). In certain embodiments, an extended oligonucleotide comprising a capture agent is captured by contacting a binding pair member with a solid phase comprising the other member of the binding pair (e.g., avidin/streptavidin or biotin). In certain embodiments an extended oligonucleotide is biotinylated, and the biotin moiety with extended oligonucleotide product is captured by contacting the biotin moiety with an avidin or streptavidin coated solid phase. In some embodiments, an extended oligonucleotide comprises a mass distinguishable tag or other label, and in certain embodiments, detecting the mass distinguishable tag or other label comprises detecting the presence or absence of an extended oligonucleotide. In some embodiments, an extended oligonucleotide bound to a solid phase is released from the solid phase by competition with a competitor and the extended oligonucleotide is detected. In some embodiments, an extended oligonucleotide bound to a solid phase is released from the solid phase by competition with a competitor and a distinguishable label in, or associated with, the extended oligonucleotide is detected. In some embodiments, an extended oligonucleotide bound to a solid phase is released from the solid phase by competition with a competitor, a distinguishable label is released from the extended oligonucleotide, and the released distinguishable label is detected.

Distinguishable Labels, Detection and Release

As used herein, the terms "distinguishable labels" and "distinguishable tags" refer to types of labels or tags that can be distinguished from one another and used to identify the nucleic acid to which the tag is attached. A variety of types of labels and tags may be selected and used for multiplex methods provided herein. For example, oligonucleotides, amino acids, small organic molecules, light-emitting molecules, light-absorbing molecules, light-scattering molecules, luminescent molecules, isotopes, enzymes and the like may be used as distinguishable labels or tags. In certain embodiments, oligonucleotides, amino acids, and/or small molecule organic molecules of varying lengths, varying mass-to-charge ratios, varying electrophoretic mobility (e.g., capillary electrophoresis mobility) and/or varying mass also can be used as distinguishable labels or tags. Accordingly, a fluorophore, radioisotope, colormetric agent, light emitting agent, chemiluminescent agent, light scattering agent, and the like, may be used as a label. The choice of label may depend on the sensitivity required, ease of conjugation with a nucleic acid, stability requirements, and available instrumentation. The term "distinguishable feature," as used herein with respect to distinguishable labels and tags, refers to any feature of one label or tag that can be distinguished from another label or tag (e.g., mass and others described herein). In some embodiments the label is attached to the chain terminating nucleotide. In some embodiments, label composition of the distinguishable labels and tags can be selected and/or designed to result in optimal flight behavior in a mass spectrometer and to allow labels and tags to be distinguished at high multiplexing levels. In some embodiments, labels such as fluorescent labels are utilized with a method that achieves separation in space, such as an array, beads or capillary electrophoresis.

Detectable labels include, but are not limited to, nucleotides (labeled or unlabelled), compomers, sugars, peptides, proteins, antibodies, chemical compounds, conducting polymers, binding moieties such as biotin, mass tags, iron oxide particles or beads, colorimetric agents, light emitting agents, chemiluminescent agents, light scattering agents, fluorescent tags, radioactive tags, charge tags (electrical or magnetic charge), volatile tags and hydrophobic tags, biomolecules (e.g., members of a binding pair antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) and the like, some of which are further described below. In some embodiments a probe may contain a signal-generating moiety that hybridizes to a target and alters the passage of the target nucleic acid through a nanopore, and can generate a signal when released from the target nucleic acid when it passes through the nanopore (e.g., alters the speed or time through a pore of known size).

The term "detection" of a label as used herein refers to identification of a label species. Any suitable detection device can be used to distinguish label species in a sample. Detection devices suitable for detecting mass distinguishable labels, include, without limitation, certain mass spectrometers and gel electrophoresis devices. Examples of mass spectrometry formats include, without limitation, Matrix-Assisted Laser Desorption/Ionization Time-of-Flight (MALDI-TOF) Mass Spectrometry (MS), MALDI orthogonal TOF MS (OTOF MS; two dimensional), Laser Desorption Mass Spectrometry (LDMS), Electrospray (ES) MS, Ion Cyclotron Resonance (ICR) MS, and Fourier Transform MS. Methods described herein are readily applicable to mass spectrometry formats in which analyte is volatized and ionized ("ionization MS," e.g., MALDI-TOF MS, LDMS, ESMS, linear TOF, OTOF). Orthogonal ion extraction MALDI-TOF and axial MALDI-TOF can give rise to relatively high resolution, and thereby, relatively high levels of multiplexing. Detection devices suitable for detecting light-emitting, light absorbing and/or light-scattering labels, include, without limitation, certain light detectors and photodetectors (e.g., for fluorescence, chemiluminescence, absorbtion, and/or light scattering labels).

The labeled extension products corresponding to the low-abundance (minor) and high-abundance (major) variants can be analyzed by a variety of methods including, but not limited to, mass spectrometry, MALDI-TOF mass spectrometry, fluorescence detection, DNA sequencing gel, capillary electrophoresis on an automated DNA sequencing machine, microchannel electrophoresis, and other methods of sequencing, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry, measurement of current/electrochemical signal or by DNA hybridization techniques including Southern Blots, Slot Blots, Dot Blots, and DNA microarrays, wherein DNA fragments would be useful as both "probes" and "targets," ELISA, fluorimetry, Fluorescence Resonance Energy Transfer (FRET), SNP-IT, GeneChips, HuSNP, BeadArray, TaqMan assay, Invader assay, MassExtend®, or MassCleave® method.

The extension products corresponding to the high-abundance variants (major variants) and the low-abundance variants (minor variants) that are obtained by the methods provided herein can be detected by a variety of methods. For example, the extension primers (UEPs) and/or the chain terminating reagents may be labeled with any type of chemical group or moiety that allows for detection of a signal and/or quantification of the signal including, but not limited to, mass labels, radioactive molecules, fluorescent molecules, antibodies, antibody fragments, haptens, carbohydrates, biotin, derivatives of biotin, phosphorescent moieties, luminescent moieties, electrochemiluminescent moieties, moieties that generate an electrochemical signal upon oxidation or reduction, e.g., complexes of iron, ruthenium or osmium (see, for example, eSensor technology used by Genmark Diagnostics, Inc. e.g., as described in Peirce et al., J. Clin. Micribiol., 50(11):3458-3465 (2012)), chromatic moieties, and moieties having a detectable electron spin resonance, electrical capacitance, dielectric constant or electrical conductivity, or any combination of labels thereof.

For methods used herein, a particular target nucleic acid species, amplicon species and/or extended oligonucleotide species often is paired with a distinguishable detectable label species, such that the detection of a particular label or tag species directly identifies the presence of a particular target nucleic acid species, amplicon species and/or extended oligonucleotide species in a particular composition. Accordingly, one distinguishable feature of a label species can be used, for example, to identify one target nucleic acid species in a composition, as that particular distinguishable feature corresponds to the particular target nucleic acid. Labels and tags may be attached to a nucleic acid (e.g., oligonucleotide) by any known methods and in any location (e.g., at the 5' of an oligonucleotide). Thus, reference to each particular label species as "specifically corresponding" to each particular target nucleic acid species, as used herein, refers to one label species being paired with one target species. When the presence of a label species is detected, then the presence of the target nucleic acid species associated with that label species thereby is detected, in certain embodiments.

The term "species," as used herein with reference to a distinguishable tag or label (collectively, "label"), refers to one label that is detectably distinguishable from another label. In certain embodiments, the number of label species, includes, but is not limited to, about 2 to about 10000 label species, about 2 to about 500,000 label species, about 2 to about 100,000, about 2 to about 50000, about 2 to about 10000, and about 2 to about 500 label species, or sometimes about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000 or 500000 label species.

The term "mass distinguishable label" as used herein refers to a label that is distinguished by mass as a feature. The distinguishable tag in some embodiments consists of nucleotides, and sometimes the tag is about 5 nucleotides to about 50 nucleotides in length. The distinguishable tag in certain embodiments is a nucleotide compomer, which sometimes is about 5 nucleotides to about 35 nucleotides in length. In some embodiments, the distinguishable tag is a peptide, which sometimes is about 5 amino acids to about 100 amino acids in length. The distinguishable tag in certain embodiments is a concatemer of organic molecule units. In some embodiments, the tag is a trityl molecule concatemer.

A variety of mass distinguishable labels can be selected and used, such as for example a compomer, amino acid and/or a concatemer. Different lengths and/or compositions of nucleotide strings (e.g., nucleic acids; compomers), amino acid strings (e.g., peptides; polypeptides; compomers) and/or concatemers can be distinguished by mass and be used as labels. Any number of units can be utilized in a mass distinguishable label, and upper and lower limits of such units depends in part on the mass window and resolution of the system used to detect and distinguish such labels. Thus, the length and composition of mass distinguishable labels can be selected based in part on the mass window and resolution of the detector used to detect and distinguish the labels.

The term "compomer" as used herein refers to the composition of a set of monomeric units and not the particular sequence of the monomeric units. For a nucleic acid, the term "compomer" refers to the base composition of the nucleic acid with the monomeric units being bases. The number of each type of base can be denoted by Bn (i.e.: AaCcGgTt, with A0C0G0T0 representing an "empty" compomer or a compomer containing no bases). A natural compomer is a compomer for which all component monomeric units (e.g., bases for nucleic acids and amino acids for polypeptides) are greater than or equal to zero. In certain embodiments, at least one of a, c, g or t equals 1 or more (e.g., A0C0G1T0, A1C0G1T0, A2C1G1T2, A3C2G1T5). For purposes of comparing sequences to determine sequence variations, in the methods provided herein, "unnatural" compomers containing negative numbers of monomeric units can be generated by an algorithm utilized to process data. For polypeptides, a compomer refers to the amino acid composition of a polypeptide fragment, with the number of each type of amino acid similarly denoted. A compomer species can correspond to multiple sequences. For example, the compomer A2G3 corresponds to the sequences AGGAG, GGGAA, AAGGG, GGAGA and others. In general, there is a unique compomer corresponding to a sequence, but more than one sequence can correspond to the same compomer. In certain embodiments, one compomer species is paired with (e.g., corresponds to) one target nucleic acid species, amplicon species and/or oligonucleotide species. Different compomer species have different base compositions, and distinguishable masses, in embodiments herein (e.g., A0C0G5T0 and A0C5G0T0 are different and mass-distinguishable compomer species). In some embodiments, a set of compomer species differ by base composition and have the same length. In certain embodiments, a set of compomer species differ by base compositions and length.

A nucleotide compomer used as a mass distinguishable label can be of any length for which all compomer species can be detectably distinguished, for example about 1 to 15, 5 to 20, 1 to 30, 5 to 35, 10 to 30, 15 to 30, 20 to 35, 25 to 35, 30 to 40, 35 to 45, 40 to 50, or 25 to 50, or sometimes about 55, 60, 65, 70, 75, 80, 85, 90, 85 or 100, nucleotides in length. A peptide or polypeptide compomer used as a mass distinguishable label can be of any length for which all compomer species can be detectably distinguished, for example about 1 to 20, 10 to 30, 20 to 40, 30 to 50, 40 to 60, 50 to 70, 60 to 80, 70 to 90, or 80 to 100 amino acids in length. As noted above, the limit to the number of units in a compomer often is limited by the mass window and resolution of the detection method used to distinguish the compomer species.

The terms "concatemer" and "concatemer" are used herein synonymously (collectively "concatemer"), and refer to a molecule that contains two or more units linked to one another (e.g., often linked in series; sometimes branched in certain embodiments). A concatemer sometimes is a nucleic acid and/or an artificial polymer in some embodiments. A concatemer can include the same type of units (e.g., a homoconcatemer) in some embodiments, and sometimes a concatemer can contain different types of units (e.g., a heteroconcatemer). A concatemer can contain any type of unit(s), including nucleotide units, amino acid units, small organic molecule units (e.g., trityl), particular nucleotide sequence units, particular amino acid sequence units, and the like. A homoconcatemer of three particular sequence units ABC is ABCABCABC, in an embodiment. A concatemer can contain any number of units so long as each concatemer species can be detectably distinguished from other species. For example, a trityl concatemer species can contain about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 80, 85, 90, 95, 100, 125, 150, 175, 200, 225, 250, 275, 300, 325, 350, 375, 400, 425, 450, 475, 500, 600, 700, 800, 900 or 1000 trityl units, in some embodiments.

A distinguishable label can be released from a nucleic acid product (e.g., an extended oligonucleotide) in certain embodiments. The linkage between the distinguishable label and a nucleic acid can be of any type that can be transcribed and cleaved, cleaved and allow for detection of the released label or labels (e.g., U.S. patent application publication no. US20050287533A1, entitled "Target-Specific Compomers and Methods of Use," naming Ehrich et al.). Such linkages and methods for cleaving the linkages ("cleaving conditions") are known. In certain embodiments, a label can be separated from other portions of a molecule to which it is attached. In some embodiments, a label (e.g., a compomer) is cleaved from a larger string of nucleotides (e.g., extended oligonucleotides). Non-limiting examples of linkages include linkages that can be cleaved by a nuclease (e.g., ribonuclease, endonuclease); linkages that can be cleaved by a chemical; linkages that can be cleaved by physical treatment; and photocleavable linkers that can be cleaved by light (e.g., o-nitrobenzyl, 6-nitroveratryloxycarbonyl, 2-nitrobenzyl group). Photocleavable linkers provide an advantage when using a detection system that emits light (e.g., matrix-assisted laser desorption ionization (MALDI) mass spectrometry involves the laser emission of light), as cleavage and detection are combined and occur in a single step.

In certain embodiments, a label can be part of a larger unit, and can be separated from that unit prior to detection. For example, in certain embodiments, a label is a set of contiguous nucleotides in a larger nucleotide sequence, and the label is cleaved from the larger nucleotide sequence. In such embodiments, the label often is located at one terminus of the nucleotide sequence or the nucleic acid in which it resides. In some embodiments, the label, or a precursor thereof, resides in a transcription cassette that includes a promoter sequence operatively linked with the precursor sequence that encodes the label. In the latter embodiments, the promoter sometimes is a RNA polymerase-recruiting promoter that generates an RNA that includes or consists of the label. An RNA that includes a label can be cleaved to release the label prior to detection (e.g., with an RNase).

In certain embodiments, a distinguishable label or tag is not cleaved from an extended oligonucleotide, and in some embodiments, the distinguishable label or tag comprises a capture agent. In certain embodiments, detecting a distinguishable feature includes detecting the presence or absence of an extended oligonucleotide, and in some embodiments an extended oligonucleotide includes a capture agent. In some embodiments an extended oligonucleotide is released from a solid phase by competition with a competitor, and in certain embodiments competition with a competitor comprises contacting a solid phase with a competitor. In some embodiments, releasing an extended oligonucleotide from a solid phase is carried out under elevated temperature conditions. In certain embodiments, the elevated temperature conditions are between about 80 degrees Celsius and about 100 degrees Celsius. In some embodiments, releasing the extend oligonucleotides from the capture agent occurs under elevated temperature conditions for between about 1 minute and about 10 minutes. In certain embodiments, releasing an extended oligonucleotides from a solid phase includes treatment with a competitor (e.g., free capture agent, competing fragment of free capture agent, multimer of free capture agent, any molecule that specifically competes for binding to the solid phase, the like and combinations thereof) for about 5 minutes at about 90 degrees Celsius. In some embodiments, a competitor is biotin and a solid phase comprises avidin/streptavidin, and in certain embodiments a competitor is avidin/streptavidin and a solid phase comprises biotin.

In certain embodiments, a multiplex assay includes some oligonucleotides that are extended and some oligonucleotides that are not extended after extension. In such embodiments, oligonucleotides that are not extended often do not bind to a solid phase.

In some embodiments, the ratio of competitor to capture agent attached to a nucleotide or nucleic acid (e.g., extended oligonucleotide with incorporated capture agent (e.g., biotin)) can be 1:1. In certain embodiments, a competitor may be used in excess of capture agent associated with an oligonucleotide, and in some embodiments, capture agent associated with an oligonucleotide may be in excess of competitor. In such embodiments, the excess sometimes is about a 5-fold excess to about a 50,000-fold excess (e.g., about a 10-fold excess, about a 100-fold excess, about a 1,000-fold excess, or about a 10,000-fold excess).

Multiplexing

Methods provided herein allow for high-throughput detection and quantification of target nucleic acid species in a plurality of target nucleic acids and their high-abundance and low-abundance variants. Multiplexing refers to the simultaneous detection of more than one target nucleic acid species. General methods for performing multiplexed reactions in conjunction with mass spectrometry, are known (see, e.g., U.S. Pat. Nos. 6,043,031, 5,547,835 and International PCT application No. WO 97/37041). Multiplexing provides an advantage that a plurality of target nucleic acid species and variants thereof (e.g., some having different sequence variations) can be identified in as few as a single mass spectrum, as compared to having to perform a separate mass spectrometry analysis for each individual target nucleic acid species. Methods provided herein lend themselves to high-throughput, highly-automated processes for analyzing sequence variations with high speed and accuracy, in some embodiments. In some embodiments, methods herein may be multiplexed at high levels in a single reaction. Multiplexing is applicable when the genotype at a polymorphic locus is not known, and in some embodiments, the genotype at a locus is known. In some embodiments, multiplexing utilizes described detection methods other than mass spectrometry.

In certain embodiments, the number of target nucleic acid species multiplexed include, without limitation, about 2 to 1,000 species, and sometimes about 1-3, 3-5, 5-7, 7-9, 9-11, 11-13, 13-15, 15-17, 17-19, 19-21, 21-23, 23-25, 25-27, 27-29, 29-31, 31-33, 33-35, 35-37, 37-39, 39-41, 41-43, 43-45, 45-47, 47-49, 49-51, 51-53, 53-55, 55-57, 57-59, 59-61, 61-63, 63-65, 65-67, 67-69, 69-71, 71-73, 73-75, 75-77, 77-79, 79-81, 81-83, 83-85, 85-87, 87-89, 89-91, 91-93, 93-95, 95-97, 97-101, 101-103, 103-105, 105-107, 107-109, 109-111, 111-113, 113-115, 115-117, 117-119, 121-123, 123-125, 125-127, 127-129, 129-131, 131-133, 133-135, 135-137, 137-139, 139-141, 141-143, 143-145, 145-147, 147-149, 149-151, 151-153, 153-155, 155-157, 157-159, 159-161, 161-163, 163-165, 165-167, 167-169, 169-171, 171-173, 173-175, 175-177, 177-179, 179-181, 181-183, 183-185, 185-187, 187-189, 189-191, 191-193, 193-195, 195-197, 197-199, 199-201, 201-203, 203-205, 205-207, 207-209, 209-211, 211-213, 213-215, 215-217, 217-219, 219-221, 221-223, 223-225, 225-227, 227-229, 229-231, 231-233, 233-235, 235-237, 237-239, 239-241, 241-243, 243-245, 245-247, 247-249, 249-251, 251-253, 253-255, 255-257, 257-259, 259-261, 261-263, 263-265, 265-267, 267-269, 269-271, 271-273, 273-275, 275-277, 277-279, 279-281, 281-283, 283-285, 285-287, 287-289, 289-291, 291-293, 293-295, 295-297, 297-299, 299-301, 301-303, 303-305, 305-307, 307-309, 309-311, 311-313, 313-315, 315-317, 317-319, 319-321, 321-323, 323-325, 325-327, 327-329, 329-331, 331-333, 333-335, 335-337, 337-339, 339-341, 341-343, 343-345, 345-347, 347-349, 349-351, 351-353, 353-355, 355-357, 357-359, 359-361, 361-363, 363-365, 365-367, 367-369, 369-371, 371-373, 373-375, 375-377, 377-379, 379-381, 381-383, 383-385, 385-387, 387-389, 389-391, 391-393, 393-395, 395-397, 397-401, 401-403, 403-405, 405-407, 407-409, 409-411, 411-413, 413-415, 415-417, 417-419, 419-421, 421-423, 423-425, 425-427, 427-429, 429-431, 431-433, 433-435, 435-437, 437-439, 439-441, 441-443, 443-445, 445-447, 447-449, 449-451, 451-453, 453-455, 455-457, 457-459, 459-461, 461-463, 463-465, 465-467, 467-469, 469-471, 471-473, 473-475, 475-477, 477-479, 479-481, 481-483, 483-485, 485-487, 487-489, 489-491, 491-493, 493-495, 495-497, 497-501 species or more.

Design methods for achieving resolved mass spectra with multiplexed assays can include primer and oligonucleotide design methods and reaction design methods. For primer and oligonucleotide design in multiplexed assays, the same general guidelines for primer design applies for uniplexed reactions, such as avoiding false priming and primer dimers, only more primers are involved for multiplex reactions. In addition, analyte peaks in the mass spectra for one assay are sufficiently resolved from a product of any assay with which that assay is multiplexed, including pausing peaks and any other by-product peaks. Also, analyte peaks optimally fall within a user-specified mass window, for example, within a range of 5,000-8,500 Da. Extension oligonucleotides can be designed with respect to target sequences of a given SNP strand, in some embodiments. In such embodiments, the length often is between limits that can be, for example, user-specified (e.g., 17 to 24 bases or 17 to 26 bases) and often do not contain bases that are uncertain in the target sequence. Hybridization strength sometimes is gauged by calculating the sequence-dependent melting (or hybridization/dissociation) temperature, Tm. A particular primer choice may be disallowed, or penalized relative to other choices of primers, because of its hairpin potential, false priming potential, primer-dimer potential, low complexity regions, and problematic subsequences such as GGGG. Methods and software for designing extension oligonucleotides (e.g., according to these criteria) are known, and include, for example, SpectroDESIGNER (Sequenom). Multiplex assays are designed such that target nucleic acid species included in the same plex have a common low-abundance variant (i.e., same mutant genotype).

In some embodiments, multiplex assays provided herein are designed for single base extension and the target nucleic acid species included in the same plex have a common low-abundance variant. Assays are designed in part utilizing the following criteria:

a. An oligonucleotide species hybridizes to amplicons derived from the low-abundance variant and the high-abundance variant of a target nucleic acid species at a position 5' to a single base position that differs between the low-abundance variant and the high-abundance variant of the target nucleic acid species.

b. The nucleotide at the single base position is the same or different for each of the high-abundance variants of the plurality of target nucleic acid species in the plex.

c. The nucleotide at the single base position is the same for each of the low-abundance variants of the plurality of target nucleic acid species in the plex (i.e., all assays in a plex have the same low abundance or mutant base in common).

d. The nucleotide(s) at the single base position for the high-abundance variants of the plurality of target nucleic acid species are not the same as the nucleotide at the single base position for the low-abundance variants of the plurality of target nucleic acid species in the plex.

The multiplex assays are based on using a single terminating nucleotide specific for extending the low-abundance variants of the target nucleic acid species included in a single plex. The multiplex assays can include one, two or three different terminating nucleotides specific for extending the high frequency variants of the target nucleic acid species in the assay. For example, if the low-abundance variants are extended by a ddTTP, the extension mix can include one, two or three of ddATP, ddGTP and ddCTP.

Four multiplex assays (plexes) are designed with each plex targeting a different low-abundance variant. Target nucleic acid species that have the same low-abundance variant are combined in a single plex.

Multiplex C
　Low-abundance variant—C
　Possible high-abundance variants—G, A, T
Multiplex A
　Low-abundance variant A
　Possible high-abundance variants—G, C, T
Multiplex T
　Low-abundance variant T
　Possible high-abundance variants—G, A, C
Multiplex G
　Low-abundance variant G
　Possible high-abundance variants—C, A, T Each low-abundance variant is interrogated in the forward and reverse direction to facilitate the requirement of all possible high-abundance variant/low-abundance variant combinations. The design avoids overlap from extension oligonucleotide and PCR primer so as to avoid any potential exonuclease derived additional signals As used herein, the term "call rate" or "calling rate" refers to the number of calls (e.g., genotypes determined) obtained relative to the number of calls attempted to be obtained. In other words, for a 12-plex reaction, if 10 genotypes are ultimately determined from conducting methods provided herein, then 10 calls have been obtained with a call rate of 10/12. Different events can lead to failure of a particular attempted assay, and lead to a call rate lower than 100%. Occasionally, in the case of a mix of dNTPs and ddNTPs for termination, inappropriate extension products can occur by pausing of a polymerase after incorporation of one non-terminating nucleotide (i.e., dNTP), resulting in a prematurely terminated extension primer, for example. The mass difference between this falsely terminated and a correctly terminated primer mass extension reaction at the polymorphic site sometimes is too small to resolve consistently and can lead to miscalls if an inappropriate termination mix is used. The mass differences between a correct termination and a false termination (i.e., one caused by pausing) as well between a correct termination and salt adducts as well as a correct termination and an unspecific incorporation often is maximized to reduce the number of miscalls.

Multiplex assay accuracy may be determined by assessing the number of calls obtained (e.g., correctly or accurately assessed) and/or the number of false positive and/or false negative events in one or more assays. Accuracy also may be assessed by comparison with the accuracy of corresponding uniplex assays for each of the targets assessed in the multiplex assay. In certain embodiments, one or more methods may be used to determine a call rate. For example, a manual method may be utilized in conjunction with an automated or computer method for making calls, and in some embodiments, the rates for each method may be summed to calculate an overall call rate. In certain embodiments, accuracy or call rates, when multiplexing two or more target nucleic acids (e.g., fifty or more target nucleic acids), can be about 99% or greater, 98%, 97%, 96%, 95%, 94%, 93%, 92%, 91%, 90%, 89%, 87-88%, 85-86%, 83-84%, 81-82%, 80%, 78-79% or 76-77%, for example. In some embodiments, a call rate for each target species in a multiplex assay that includes about 2 to 200 target species is greater than or equal to 80% or more (e.g., 81%, 82%, 83%, 84%, 85%, 86%, 87%, 88%, 89%, 90%, 91%, 92%, 93%, 94%, 95%, 96%, 97%, 98%, 99% or greater).

In certain embodiments the error rate may be determined based on the call rate or rate of accuracy. For example, the error rate may be the number of calls made in error. In some embodiments, for example, the error rate may be 100% less the call rate or rate of accuracy. The error rate may also be referred to as the "fail rate." Identification of false positives and/or false negatives can readjust both the call and error rates. In certain embodiments running more assays can also help in identifying false positives and/or false negatives, thereby adjusting the call and/or error rates. In certain embodiments, error rates, when multiplexing two or more target nucleic acids (e.g., fifty or more target nucleic acids), can be about 1% or less, 2%, 3%, 4,%, 5%, 6%, 7%, 8%, 9%, 10%, 11%, 12%, 13%, 14%, 15%, 16%, 17%, 18%, 19%, 20%, 21%, 22%, 23%, 24% or 25%, for example.

EXAMPLES

The examples set forth below illustrate, and do not limit the technology.

Example 1

Skewed Terminator Variant Detection

The following method uses skewed concentrations of terminators directed to low-abundance variants and high abundance variants as previously described herein to interrogate multiple informative variants within a single reaction.

Assay Design

Each assay consists of three primers, two PCR primers and one single base extension primer. All amplicons are under 150 bp in length to ensure amplification success in circulating cell free DNA and mass tags are added to the 5' end of the primer to move unincorporated PCR primers out of the analytical mass window. Extension probe design also has few requirements. First, the mass of the extended products must be sufficiently spaced by mass to ensure no conflicts between assays. Second, multiplexing is based on mutant allele (low-abundance variant) hence in one reaction only minor allele variants (low-abundance variants) with an identical nucleotide incorporated during the single base extension are multiplexed together. No concern is taken to the major allele (high-abundance variant) as long as it is different from the minor allele. The extension product for the major allele (high-abundance variant) provides a control for distinguishing a wild type result from a failed assay. Optional control assays, for example, can include capture controls to verify that the bead capture, cleaning, and elution steps were successful.

PCR Amplification

PCR is carried out in a total volume of 20 μL with 10 μL of DNA template supplemented with 10 μL of a master mix consisting of 1×PCR Buffer supplemented with 1 mM $MgCl_2$, 125 μM dNTPs, 0.125 U Uracil-DNA glycosylase (New England Biolabs®, Ipswich, Mass., USA), 4 U Taq polymerase, and 100 nM of each PCR primer. Reactions are initially incubated at 30° C. for 10 minutes followed by 94° C. for 2 minutes. 45 cycles of PCR were performed at 94° C. for 30 seconds, 56° C. for 30 seconds, and 72° C. for 1 minute. The PCR is completed with a final incubation of 5 minutes at 72° C. 5 μL of amplified products are conditioned with the addition of 2 μL of 0.5 U shrimp alkaline phosphatase (SAP) in 0.24×SAP buffer in a total volume of 7 μL for 40 minutes at 37° C. followed by SAP enzyme denaturation for 10 minutes at 85° C.

Single Base Extension

Single base extension is performed by adding 2 μL of a mastermix consisting of 0.2× extension buffer, 5.56 μM of the minor allele variant nucleotide and different concentrations of the major allele variant nucleotides ranging from 0.03-1.25 μM, extension primers at various concentrations, and 0.14 U iPLEX® Pro enzyme. Single base extension reactions are performed in a total volume of 9 μL. Reaction parameters include an initial incubation at 94° C. for 30 seconds followed by 40 cycles at 94° C. for 5 seconds with five nested cycles of 52° C. for 5 seconds then 80° C. for 5 seconds. The single base extension is completed with an incubation at 72° C. for 3 minutes.

Capture and Data Acquisition

Prior to capture, the streptavidin coated magnetic beads are conditioned in binding and wash buffer. Two rounds of conditioning are performed on the beads and then they are re-suspended in the binding and wash buffer at a concentration of 1 μg/μL. A total volume of 41 μL of conditioned beads is added to each 9 μL reaction and capture is performed at room temperature for 30 minutes under constant rotation. Beads with captured products are pelleted using a magnet and the binding and wash solution is removed. The beads are washed once with 100 μL of HPLC grade water, re-suspended with 13 μL of elution solution (free biotin in solution), and incubated at 95° C. for 5 min. Eluted products are conditioned with 5 μL (3 mg) of anion exchange resin slurry. The analyte is dispensed onto a Spectrochip® II solid support using an RS1000 Nanodispenser. Data is acquired via MALDI-TOF mass spectrometry using the MassARRAY® 4 instrument.

Examples of Embodiments

Listed hereafter are non-limiting examples of certain embodiments of the technology.

A1. A multiplex method for detecting the presence or absence of variants of a plurality of nucleic acid species, comprising:
(a) preparing a plurality of amplicons derived from a plurality of target nucleic acid species, or portions thereof, wherein each target nucleic acid species comprises a low-abundance variant and a high-abundance variant;
(b) in a single reaction hybridizing the amplicons to a plurality of oligonucleotide species, each oligonucleotide species specifically corresponds to amplicons of a target nucleic acid species, wherein (i) an oligonucleotide species hybridizes to amplicons derived from the low-abundance variant and the high-abundance variant of a target nucleic acid species at a position 5' to a single base position that differs between the low-abundance variant and the high-abundance variant of the target nucleic acid species, (ii) the nucleotide at the single base position is the same or different for each of the high-abundance variants of the plurality of target nucleic acid species, (iii) the nucleotide at the single base position is the same for each of the low-abundance variants of the plurality of target nucleic acid species and (iv) none of the nucleotides at the single base positions for the high-abundance variants of the plurality of target nucleic acid species are the same as the nucleotide at the single base position for the low-abundance variants of the plurality of target nucleic acid species; thereby generating hybridized oligonucleotides; and (c) contacting the hybridized oligonucleotides with an extension composition comprising a terminating nucleotide specific for the low-abundance variants and one, two or three terminating nucleotides specific for one or more of the high-abundance variants under extension conditions; wherein: (i) the terminating nucleotides comprises a capture agent, (ii) the concentration of the one, two or three terminating nucleotides specific for one or more high-abundance variants are each at a concentration of from 0.1% to 30% relative to the concentration of the terminating nucleotide specific for the low-abundance variants, (iii) the extension conditions comprise multiple thermal cycles, thereby generating extended oligonucleotides comprising a terminating nucleotide specific for the low-abundance variants of the plurality of target nucleic acid species and extended oligonucleotides comprising a terminating nucleotide specific for the high-abundance variants of the plurality of target nucleic acid species;

(d) contacting the extended oligonucleotides with a solid phase under conditions in which the capture agent interacts with the solid phase, thereby capturing the extended oligonucleotides onto the solid phase, wherein the solid phase comprises a binding partner of the capture agent in (c);

(e) releasing the extended oligonucleotides in (d) by contacting the solid phase at elevated temperature conditions with a competitor, wherein the competitor comprises the free form of the capture agent that interacts with the solid phase in (d); and (f) detecting the extended oligonucleotides released in (e); thereby detecting the presence or absence of the variants of a plurality of nucleic acid species.

A2. The method of embodiment A1, wherein the variants are single nucleotide polymorphism (SNP) variants, the low-abundance variant is a lower-abundance allele and the high-abundance variant is a higher-abundance allele.

A3. The method of embodiment A1, wherein the low-abundance variant is a mutant allele and the high-abundance variant is the wild type of the allele.

A3.1 The method of embodiment A1, wherein the low-abundance variant has one or more insertions or a deletions and the high-abundance variant does not have one or more insertions or deletions.

A4. The method of any one of embodiments A1 to A3.1, wherein the low-abundance variant is present in a copy number that is 2% or less than the copy number of the high-abundance variant.

A4.1. The method of any one of embodiments A1 to A4, wherein the low-abundance variant is present in a copy number that is 1% or less than the copy number of the high-abundance variant.

A4.2. The method of any one of embodiments A1 to A4.1, wherein the low-abundance variant is present in a copy number that is 0.1% relative to the copy number of the high-abundance variant.

A5. The method of any one of embodiments A1 to A4.2, wherein the one or more terminating nucleotides specific for the high-abundance variants consist of one terminating nucleotide.

A6. The method of any one of embodiments A1 to A4.2, wherein the one or more terminating nucleotides specific for the high-abundance variants consist of two different terminating nucleotides.

A7. The method of any one of embodiments A1 to A4.2, wherein the one or more terminating nucleotides specific for the high-abundance variants consist of three different terminating nucleotides.

A8. The method of any one of embodiments A1 to A7, wherein the terminating nucleotides independently are selected from ddATP, ddGTP, ddCTP, ddTTP and ddUTP.

A9. The method of any one of embodiments A1 to A7, wherein the terminating nucleotides comprise one or more acyclic terminators.

A9.1 The method of any of embodiments A1 to A9, wherein the concentration of each of the one, two or three terminating nucleotides specific for the high-abundance variants is at a concentration of from 0.5% to 10% relative to the concentration of the specific terminating nucleotide for the low-abundance variants.

A9.2 The method of any of embodiments A1 to A9, wherein the concentration of each of the one, two or three terminating nucleotides specific for the high-abundance variants is at a concentration of from 1% to 2% relative to the concentration of the specific terminating nucleotide for the low-abundance variants.

A10. The method of any of embodiments A1 to A9.2, wherein for each nucleic acid species the total copy number of the low-abundance variant and the high-abundance variant is at least about 1000 copies and the low-abundance variant represents 0.1% of the total copy number.

A11. The method of any one of embodiments A1 to A10, wherein the amplicons produced in (a) are contacted with an agent that removes terminal phosphates from any nucleotides not incorporated into the amplicons.

A12. The method of any one of embodiments A1 to A11, wherein the terminal phosphate is removed by contacting the solution with a phosphatase.

A13. The method of embodiment A12, wherein the phosphatase is alkaline phosphatase.

A14. The method of embodiment A13, wherein the alkaline phosphatase is shrimp alkaline phosphatase.

A15. The method of any one of embodiments A1 to A14, wherein the plurality of target nucleic acid species is 10 or more target nucleic acid species.

A16. The method of any one of embodiments A1 to A14, wherein the plurality of target nucleic acid species is 20 or more target nucleic acid species.

A17. The method of any one of embodiments A1 to A6, wherein the extension conditions in (a) comprise cycling 30 to 45 times.

A18. The method of any one of embodiments A1 to A17, wherein the extension conditions in (c) comprise cycling 20 to 300 times.

A19. The method of any one of embodiments A1 to A17, wherein the extension conditions in (c) comprise cycling at least 50 times.

A20. The method of any one of embodiments A1 to A19, wherein the capture agent comprises avidin, an analogue of avidin, streptavidin, an analogue of streptavidin, biotin or an analogue of biotin.

A21. The method of any one of embodiments A1 to A20, wherein the binding partner is selected from the group consisting of avidin, an analogue of avidin, streptavidin, an analogue of streptavidin, biotin or an analogue of biotin.

A22. The method of any one of embodiments A1 to A21, wherein the capture agent comprises biotin, the solid phase comprises streptavidin and the competitor comprises free biotin.

A23. The method of any one of embodiments A1 to A22, wherein the elevated temperature conditions are about 80° C. to about 100° C.

A24. The method of any of embodiments A1 to A23, wherein the elevated temperature conditions comprise treatment for about 1 minute to about 10 minutes.

A25. The method of any of embodiments A1 to A24, wherein the elevated temperature conditions comprise treatment for about 5 minutes at about 90° C.

A26. The method of any one of embodiments A1 to A25, wherein the competitor is at a concentration from about 10 ug/ml to about 100 ug/ml.

A27. The embodiment of A26, wherein the competitor is free biotin or free biotin analogue at a concentration of about 25 ug/ml.

A28. The method of any one of embodiments A1 to A27 wherein in the absence of detection of an extended oligonucleotide comprising a terminating nucleotide specific for a low-abundance variant, the detection of an extended oligonucleotide comprising a terminating nucleotide specific for a high-abundance variant provides a positive control for a false negative result.

A29. The method of any one of embodiments A1 to A28, wherein each extended oligonucleotide comprises a detectable label.

A30. The embodiment of A29, wherein the terminating nucleotide comprises the detectable label.

A31. The embodiment of A29, wherein the detectable label is a fluorescent label.

A32. The embodiment of A31, wherein a terminating nucleotide comprises the fluorescent label.

A32.1. The embodiment of A31 or A32, wherein the fluorescent label is detected by electrophoresis or real time PCR.

A33. The embodiment of A29, wherein the detectable label is a mass label.

A34. The embodiment of A33, wherein the mass label is a mass distinguishable tag that is located 5' of the region of the oligonucleotide species that hybridizes to an amplicon or the terminating nucleotide comprises the mass-distinguishable tag.

A35. The method of embodiments A33 or A34, comprising washing the solid phase after the extended oligonucleotides are captured.

A36. The embodiment of A35, wherein the washing removes salts that produce interfering adducts in mass spectrometry analysis.

A37. The method of any of embodiments A33 to A36, wherein extended oligonucleotides are not contacted with an ion exchange resin.

A38. The method of any one of embodiments of A1 to A30 and A33 to A37, wherein detection is by mass spectrometry.

A39. The method of any of embodiments A1 to A38, further comprising determining the amount of a low-abundance variant relative to the amount of a high-abundance variant for each target nucleic acid species which comprises normalization based on the ratio of the concentration of the terminating nucleotide specific for the low-abundance variant and the concentration of the terminating nucleotide specific for the high-abundance variant.

B1. A multiplex method for detecting the presence or absence and amount of variants of a plurality of nucleic acid species, comprising:

(a) preparing a plurality of amplicons derived from a plurality of target nucleic acid species, or portions thereof, wherein each target nucleic acid species comprises a low-abundance variant and a high-abundance variant;

(b) in a single reaction hybridizing the amplicons to a plurality of oligonucleotide species, each oligonucleotide species specifically corresponds to amplicons of a target nucleic acid species, wherein (i) an oligonucleotide species hybridizes to amplicons derived from the low-abundance variant and the high-abundance variant of a target nucleic acid species at a position 5' to a single base position that differs between the low-abundance variant and the high-abundance variant of the target nucleic acid species, (ii) the nucleotide at the single base position is the same or different for each of the high-abundance variants of the plurality of target nucleic acid species, (iii) the nucleotide at the single base position is the same for each of the low-abundance variants of the plurality of target nucleic acid species and (iv) none of the nucleotides at the single base positions for the high-abundance variants of the plurality of target nucleic acid species are the same as the nucleotide at the single base position for the low-abundance variants of the plurality of target nucleic acid species; thereby generating hybridized oligonucleotides; and (c) contacting the hybridized oligonucleotides with an extension composition comprising a terminating nucleotide specific for the low-abundance variants and one, two or three terminating nucleotides specific for one or more of the high-abundance variants under extension conditions; wherein: (i) the terminating nucleotides comprises a capture agent, (ii) to the concentration of the one, two or three terminating nucleotides specific for one or more high-abundance variants are each at a concentration of from 0.1% to 30% relative to the concentration of the terminating nucleotide specific for the low-abundance variants, (iii) the extension conditions comprise multiple thermal cycles, thereby generating extended oligonucleotides comprising a terminating nucleotide specific for the low-abundance variants of the plurality of target nucleic acid species and extended oligonucleotides comprising a terminating nucleotide specific for the high-abundance variants of the plurality of target nucleic acid species;

(d) contacting the extended oligonucleotides with a solid phase under conditions in which the capture agent interacts with the solid phase, thereby capturing the extended oligonucleotides onto the solid phase, wherein the solid phase comprises a binding partner of the capture agent in (c);

(e) releasing the extended oligonucleotides in (d) by contacting the solid phase at elevated temperature conditions with a competitor, wherein the competitor comprises the free form of the capture agent that interacts with the solid phase in (d);

(f) detecting the extended oligonucleotides released in (e); thereby detecting the presence or absence of the variants of the plurality of nucleic acid species, and (g) for variants of the plurality of the nucleic acid species detected as present in (f), determining the amount of the low-abundance variant relative to the amount of the high-abundance variant for each target nucleic acid species.

B2. The method of embodiment B1, wherein the variants are single nucleotide polymorphism (SNP) variants, the low-abundance variant is a lower-abundance allele and the high-abundance variant is a higher-abundance allele.

B3. The method of embodiment B1, wherein the low-abundance variant is a mutant allele and the high-abundance variant is the wild type of the allele.

B3.1 The method of embodiment B1, wherein the low-abundance variant has one or more insertions or deletions and the high-abundance variant does not have one or more insertions or deletions.

B4. The method of any one of embodiments B1 to B3.1, wherein the low-abundance variant is present in a copy number that is 2% or less than the copy number of the high-abundance variant.

B4.1. The method of any one of embodiments B1 to B4, wherein the low-abundance variant is present in a copy number that is 1% or less than the copy number of the high-abundance variant.

B4.2. The method of any one of embodiments B1 to B4.1, wherein the low-abundance variant is present in a copy number that is 0.1% relative to the copy number of the high-abundance variant.

B5. The method of any one of embodiments B1 to B4.2, wherein the one or more terminating nucleotides specific for the high-abundance variants consist of one terminating nucleotide.

B6. The method of any one of embodiments B1 to B4.2, wherein the one or more terminating nucleotides specific for the high-abundance variants consist of two different terminating nucleotides.

B7. The method of any one of embodiments B1 to B4.2, wherein the one or more terminating nucleotides specific for the high-abundance variants consist of three different terminating nucleotides.

B8. The method of any one of embodiments B1 to B7, wherein the terminating nucleotides independently are selected from ddATP, ddGTP, ddCTP, ddTTP and ddUTP.

B9. The method of any one of embodiments B1 to B7, wherein the terminating nucleotides comprise one or more acyclic terminators.

B9.1 The method of any of embodiments B1 to B9, wherein the concentration of each of the one, two or three terminating nucleotides specific for the high-abundance variants is at a concentration of from 0.5% to 10% relative to the concentration of the specific terminating nucleotide for the low-abundance variants.

B9.2. The method of any of embodiments B1 to B9, wherein the concentration of each of the one, two or three terminating nucleotides specific for the high-abundance variants is at a concentration of from 1% to 2% relative to the concentration of the specific terminating nucleotide for the low-abundance variants.

B10. The method of any of embodiments B1 to B9.2, wherein for each nucleic acid species the total copy number of the low-abundance variant and the high-abundance variant is at least about 1000 copies and the low-abundance variant represents 0.1% of the total copy number.

B11. The method of any one of embodiments B1 to B10, wherein the amplicons produced in (a) are contacted with an agent that removes terminal phosphates from any nucleotides not incorporated into the amplicons.

B12. The method of any one of embodiments B1 to B11, wherein the terminal phosphate is removed by contacting the solution with a phosphatase.

B13. The method of embodiment B12, wherein the phosphatase is alkaline phosphatase.

B14. The method of embodiment B13, wherein the alkaline phosphatase is shrimp alkaline phosphatase.

B15. The method of any one of embodiments B1 to B14, wherein the plurality of target nucleic acid species is 10 or more target nucleic acid species.

B16. The method of any one of embodiments B1 to B14, wherein the plurality of target nucleic acid species is 20 or more target nucleic acid species.

B17. The method of any one of embodiments B1 to B6, wherein the extension conditions in (a) comprise cycling 30 to 45 times.

B18. The method of any one of embodiments B1 to B17, wherein the extension conditions in (c) comprise cycling 20 to 300 times.

B19. The method of any one of embodiments B1 to B17, wherein the extension conditions in (c) comprise cycling at least 50 times.

B20. The method of any one of embodiments B1 to B19, wherein the capture agent comprises avidin, an analogue of avidin, streptavidin, an analogue of streptavidin, biotin or an analogue of biotin.

B21. The method of any one of embodiments B1 to B20, wherein the binding partner is selected from the group consisting of avidin, an analogue of avidin, streptavidin, an analogue of streptavidin, biotin or an analogue of biotin.

B22. The method of any one of embodiments B1 to B21, wherein the capture agent comprises biotin, the solid phase comprises streptavidin and the competitor comprises free biotin.

B23. The method of any one of embodiments B1 to B22, wherein the elevated temperature conditions are about 80° C. to about 100° C.

B24. The method of any of embodiments B1 to B23, wherein the elevated temperature conditions comprise treatment for about 1 minute to about 10 minutes.

B25. The method of any of embodiments B1 to B24, wherein the elevated temperature conditions comprise treatment for about 5 minutes at about 90° C.

B26. The method of any one of embodiments B1 to B25, wherein the competitor is at a concentration from about 10 ug/ml to about 100 ug/ml.

B27. The embodiment of B26, wherein the competitor is free biotin or free biotin analogue at a concentration of about 25 ug/ml.

B28. The method of any one of embodiments B1 to B27 wherein in the absence of detection of an extended oligonucleotide comprising a terminating nucleotide specific for a low-abundance variant, the detection of an extended oligonucleotide comprising a terminating nucleotide specific for a high-abundance variant provides a positive control for a false negative result.

B29. The method of any one of embodiments B1 to B28, wherein each extended oligonucleotide comprises a detectable label.

B30. The embodiment of B29, wherein the terminating nucleotide comprises the detectable label.

B31. The embodiment of B29, wherein the detectable label is a fluorescent label.

B32. The embodiment of B31, wherein a terminating nucleotide comprises the fluorescent label.

B32.1. The embodiment of B31 or B32, wherein the fluorescent label is detected by electrophoresis or real time PCR.

B33. The embodiment of B29, wherein the detectable label is a mass label.

B34. The embodiment of B33, wherein the mass label is a mass distinguishable tag that is located 5' of the region of the oligonucleotide species that hybridizes to an amplicon or the terminating nucleotide comprises the mass-distinguishable tag.

B35. The method of embodiments B33 or B34, comprising washing the solid phase after the extended oligonucleotides are captured.

B36. The embodiment of B35, wherein the washing removes salts that produce interfering adducts in mass spectrometry analysis.

B37. The method of any of embodiments B33 to B36, wherein extended oligonucleotides are not contacted with an ion exchange resin.

B38. The method of any one of embodiments of B1 to B30 and B33 to B37, wherein detection is by mass spectrometry.

B39. The method of any of embodiments B1 to B38, wherein determining the amount of a low-abundance variant relative to the amount of a high-abundance variant for each target nucleic acid species comprises normalization based on the ratio of the concentration of the terminating nucleotide specific for the low-abundance variant and the concentration of the terminating nucleotide specific for the high-abundance variant.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A multiplex method for detecting the presence or absence of variants of a plurality of nucleic acid species, comprising:
   (a) preparing a plurality of amplicons derived from a plurality of target nucleic acid species, or portions thereof, wherein each target nucleic acid species comprises a low-abundance variant and a high-abundance variant;
   (b) in a single reaction hybridizing the amplicons to a plurality of oligonucleotide species, each oligonucleotide species specifically corresponds to amplicons of a target nucleic acid species, wherein (i) an oligonucleotide species hybridizes to amplicons derived from the low-abundance variant and the high-abundance variant of a target nucleic acid species at a location whereby a single base position that differs between the low-abundance variant and the high-abundance variant of the target nucleic acid species is 3' to the hybridized oligonucleotide species, (ii) the nucleotide at the single base position is the same or different for each of the high-abundance variants of the plurality of target nucleic acid species, (iii) the nucleotide at the single base position is the same for each of the low-abundance variants of the plurality of target nucleic acid species and (iv) none of the nucleotides at the single base positions for the high-abundance variants of the plurality of target nucleic acid species are the same as the nucleotide at the single base position for the low-abundance variants of the plurality of target nucleic acid species; thereby generating hybridized oligonucleotides; and
   (c) contacting the hybridized oligonucleotides with an extension composition comprising a terminating nucleotide specific for the low-abundance variants and one, two or three terminating nucleotides specific for one or more of the high-abundance variants under extension conditions; wherein: (i) the terminating nucleotides comprises a capture agent, (ii) the concentration of the one, two or three terminating nucleotides specific for one or more high-abundance variants are each at a concentration of from 0.1% to 30% relative to the concentration of the terminating nucleotide specific for the low-abundance variants, (iii) the extension conditions comprise multiple thermal cycles, thereby generating extended oligonucleotides comprising a terminating nucleotide specific for the low-abundance variants of the plurality of target nucleic acid species and extended oligonucleotides comprising a terminating nucleotide specific for the high-abundance variants of the plurality of target nucleic acid species;
   (d) contacting the extended oligonucleotides with a solid phase under conditions in which the capture agent interacts with the solid phase, thereby capturing the extended oligonucleotides onto the solid phase, wherein the solid phase comprises a binding partner of the capture agent in (c);
   (e) releasing the extended oligonucleotides in (d) by contacting the solid phase at elevated temperature conditions with a competitor, wherein the competitor comprises the free form of the capture agent that interacts with the solid phase in (d); and (f) detecting the extended oligonucleotides released in (e); thereby detecting the presence or absence of the variants of a plurality of nucleic acid species.

2. The method of claim 1, wherein the variants are single nucleotide polymorphism (SNP) variants, the low-abundance variant is a lower-abundance allele and the high-abundance variant is a higher-abundance allele.

3. The method of claim 1, wherein the low-abundance variant is a mutant allele and the high-abundance variant is the wild type of the allele.

4. The method of claim 1, wherein the low-abundance variant has one or more insertions or a deletions and the high-abundance variant does not have one or more insertions or deletions.

5. The method of claim 1, wherein the low-abundance variant is present in a copy number that is 2% or less than the copy number of the high-abundance variant.

6. The method of claim 1, wherein the one or more terminating nucleotides specific for the high-abundance variants consist of one terminating nucleotide, two different terminating nucleotides or three different terminating nucleotides.

7. The method of claim 1, wherein the terminating nucleotides independently are selected from ddATP, ddGTP, ddCTP, ddTTP and ddUTP or comprise one or more acyclic terminators.

8. The method of claim 1, wherein the terminating nucleotides comprise one or more acyclic terminators.

9. The method of claim 1, wherein the concentration of each of the one, two or three terminating nucleotides specific for the high-abundance variants is at a concentration of from 0.5% to 10% relative to the concentration of the specific terminating nucleotide for the low-abundance variants.

10. The method of claim 1, wherein the concentration of each of the one, two or three terminating nucleotides specific for the high-abundance variants is at a concentration of from 1% to 2% relative to the concentration of the specific terminating nucleotide for the low-abundance variants.

11. The method of claim 1, wherein the amplicons produced in (a) are contacted with an agent that removes terminal phosphates from any nucleotides not incorporated into the amplicons.

12. The method of claim 1, wherein the plurality of target nucleic acid species is 10 or more target nucleic acid species or 20 or more target nucleic acid species.

13. The method of claim 1, wherein the capture agent comprises biotin, the solid phase comprises streptavidin and the competitor comprises free biotin.

14. The method of claim 13, wherein the competitor is at a concentration from about 10 ug/ml to about 100 ug/ml and the elevated temperature conditions are about 80° C. to about 100° C.

15. The method of claim 1, wherein in the absence of detection of an extended oligonucleotide comprising a terminating nucleotide specific for a low-abundance variant, the detection of an extended oligonucleotide comprising a terminating nucleotide specific for a high-abundance variant provides a positive control for a false negative result.

16. The method of claim 1, wherein each extended oligonucleotide comprises a fluorescent label and a terminating nucleotide comprises the fluorescent label.

17. The method of claim 1, wherein each extended oligonucleotide comprises a mass label and the mass label is a mass distinguishable tag that is located 5' of the region of the oligonucleotide species that hybridizes to an amplicon or the terminating nucleotide comprises the mass-distinguishable tag.

18. The method of claim 17, wherein detection is by mass spectrometry.

19. The method of claim 1, further comprising determining the amount of a low-abundance variant relative to the amount of a high-abundance variant for each target nucleic acid species which comprises normalization based on the ratio of the concentration of the terminating nucleotide specific for the low-abundance variant and the concentration of the terminating nucleotide specific for the high-abundance variant.

20. A multiplex method for detecting the presence or absence and amount of variants of a plurality of nucleic acid species, comprising:
(a) preparing a plurality of amplicons derived from a plurality of target nucleic acid species, or portions thereof, wherein each target nucleic acid species comprises a low-abundance variant and a high-abundance variant;
(b) in a single reaction hybridizing the amplicons to a plurality of oligonucleotide species, each oligonucleotide species specifically corresponds to amplicons of a target nucleic acid species, wherein (i) an oligonucleotide species hybridizes to amplicons derived from the low-abundance variant and the high-abundance variant of a target nucleic acid species at a location whereby a single base position that differs between the low-abundance variant and the high-abundance variant of the target nucleic acid species is 3' to the hybridized oligonucleotide species, (ii) the nucleotide at the single base position is the same or different for each of the high-abundance variants of the plurality of target nucleic acid species, (iii) the nucleotide at the single base position is the same for each of the low-abundance variants of the plurality of target nucleic acid species and (iv) none of the nucleotides at the single base positions for the high-abundance variants of the plurality of target nucleic acid species are the same as the nucleotide at the single base position for the low-abundance variants of the plurality of target nucleic acid species; thereby generating hybridized oligonucleotides; and
(c) contacting the hybridized oligonucleotides with an extension composition comprising a terminating nucleotide specific for the low-abundance variants and one, two or three terminating nucleotides specific for one or more of the high-abundance variants under extension conditions; wherein: (i) the terminating nucleotides comprises a capture agent, (ii) to the concentration of the one, two or three terminating nucleotides specific for one or more high-abundance variants are each at a concentration of from 0.1% to 30% relative to the concentration of the terminating nucleotide specific for the low-abundance variants, (iii) the extension conditions comprise multiple thermal cycles, thereby generating extended oligonucleotides comprising a terminating nucleotide specific for the low-abundance variants of the plurality of target nucleic acid species and extended oligonucleotides comprising a terminating nucleotide specific for the high-abundance variants of the plurality of target nucleic acid species;
(d) contacting the extended oligonucleotides with a solid phase under conditions in which the capture agent interacts with the solid phase, thereby capturing the extended oligonucleotides onto the solid phase, wherein the solid phase comprises a binding partner of the capture agent in (c);

(e) releasing the extended oligonucleotides in (d) by contacting the solid phase at elevated temperature conditions with a competitor, wherein the competitor comprises the free form of the capture agent that interacts with the solid phase in (d);
(f) detecting the extended oligonucleotides released in (e); thereby detecting the presence or absence of the variants of the plurality of nucleic acid species, and
(g) for variants of the plurality of the nucleic acid species detected as present in (f), determining the amount of the low-abundance variant relative to the amount of the high-abundance variant for each target nucleic acid species.

* * * * *